United States Patent
el Kouni et al.

[11] Patent Number: 5,773,424
[45] Date of Patent: Jun. 30, 1998

[54] TREATMENT OF TOXOPLASMOSIS

[75] Inventors: Mahmoud H. el Kouni; Vincent Guarcello; Fardos N. M. Naguib, all of Birmingham, Ala.

[73] Assignee: Research Corporation Technologies, Inc., Tucson, Ariz.

[21] Appl. No.: 358,195

[22] Filed: Dec. 16, 1994

[51] Int. Cl.$^6$ .................................................. A61K 31/70
[52] U.S. Cl. .................. 514/45; 514/24; 514/46; 514/261; 514/262
[58] Field of Search .................. 514/45, 46, 24, 514/261, 262

[56] References Cited

U.S. PATENT DOCUMENTS

| | | | |
|---|---|---|---|
| 4,786,723 | 11/1988 | Kitahara et al. | 536/27.11 |
| 4,948,783 | 8/1990 | Kawai et al. | 514/46 |
| 5,093,318 | 3/1992 | Goodman et al. | 514/45 |
| 5,254,539 | 10/1993 | Mitsuya et al. | 514/46 |

*Primary Examiner*—James O. Wilson
*Attorney, Agent, or Firm*—Scully, Scott, Murphy & Presser

[57] ABSTRACT

Pharmaceutical compositions comprising a pharmaceutical composition comprising a compound which is an α or β anomer, a D(+) or L(−) enantiomer of the following structural formula:

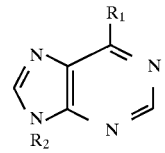

wherein, $R_1$ is a halogen, $OR_6$, $SR_6$, $SeR_6$ or $CH_2R_6$ and $R_6$ is alkyl, alkene, arylalkyl, or aryl;

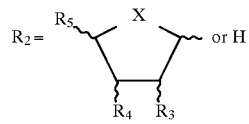

X is $CH_2$, O or S;
$R_3$ is H, OH, or a halogen;
$R_4$ is H, OH, or a halogen; and
$R_5$ is $CH_3$, $CF_3$, $CH_2OH$, or $CH_2OY$ and Y is a carbon ester or phosphorus; and
a pharmaceutically acceptable carrier.

7 Claims, No Drawings

TREATMENT OF TOXOPLASMOSIS

GOVERNMENT SUPPORT

The work resulting in this invention was supported in part by NIH Grant No. AI-29848. The U.S. government may therefore be entitled to certain rights in the invention.

BACKGROUND OF THE INVENTION

The parasitic protozoan *Toxoplasma gondii* is the etiologic agent for toxoplasmosis, a parasitic disease widespread among various warm-blooded animals, including man. Toxoplasma infection is common in man (e.g., 50% of the adult population in the U.S.), but is asymptomatic in the general population. By contrast, the disease represents a major health problem for immunocompromised individuals, such as AIDS patients, and for the unborn children of infected mothers. Toxoplasmic encephalitis has become the most common cause of intracerebral mass lesions in AIDS patients and possibly the most commonly recognized opportunistic infection of the central nervous system (Luft, B. J. and Remington, J. S. Toxoplasmic encephalitis. *J Infect Dis* 157: 1–6, 1988; McCabe, R. and Remington, J S, Toxoplasmosis: The time has come. *N. Eng. J. Med.* 318: 313–315, 1988). Congenital toxoplasmosis is as high as 1/1,000 live births, with approximately 50% of infected women giving birth to infected infants in the absence of treatment (Luft, B. J. and Remington, J. S. Toxoplasmic encephalitis. *J Infect Dis* 157: 1–6, 1988), and causes blindness, psychomotor or mental retardation, severe brain damage, or even death of infected children (McCabe, R. and Remington, J S, Toxoplasmosis: The time has come. *N. Eng. J. Med.* 318: 313–315, 1988).

In spite of the tragic consequences of toxoplasmosis, therapy for the disease has not changed materially in the last twenty years. The efficacy of the current therapy for toxoplasmosis (a combination of pyrimethamine and sulfadiazine) is limited, primarily by serious host toxicity and ineffectiveness against tissue cysts. Furthermore, as many as 50% of patients do not respond to therapy (Luft, B. J. and Remington, J. S. Toxoplasmic encephalitis. *J Infect Dis* 157: 1–6, 1988). The combination of trimethoprim and sulfamethoxazole is the only alternative therapy which has been shown to be effective in AIDS patients. However, patients who are intolerant to pyrimethamine and sulfadiazine are invariably intolerant to this alternate therapy, since both therapies have the same mechanism of action.

There is an urgent need for new and effective drugs for treating and preventing toxoplasmosis.

SUMMARY OF THE INVENTION

In one aspect, the invention features therapeutic compositions comprising purine nucleoside analogs that are selective ligands of parasite salvage pathway enzymes and a pharmaceutically acceptable carrier. Preferred purine nucleoside analogs are ligands of a parasitic adenosine kinase, nucleosidase hydrolase or phosphorylase or a purine phosphoribosyltransferase (xanthine, guanine, hypoxanthine or adenine phosphoribosyl transferase) enzyme. Particularly preferred purine analogs are D and L enantiomers, α- and β-anomers of: 6-[4-nitrobenzyl thio]-9-β-D-ribofuranosyl purine (NBMPR), 6-[4-nitrobenzyl thio]-9-β-D-ribofuranosyl purine 5'-monophosphate (NBMPR-P), 6-chloropurine riboside, 3'-deoxysangivamycin, $N^6$-(p-methoxybenzoyl)adenosine, nitrobenzyl-6-selenoriboside, $N^6$-benzyladenosine, $N^6$-azidobenzyladenosine and $N^6$-nitrobenzyladenosine, 7-deazahypoxanthine, 7-deazaxanthine, 7-deaza-6-thiopurine, 7-deaza-2-amino-6-thiopurine, and 7-deaza-2-oxo-6-thiopurines, with various substitutions on the pentose and purine moieties.

In another aspect, the invention features methods for treating a subject for a disease, which is caused by or contributed to by cells, which are dependent on a parasite salvage pathway enzymes for their purine requirement by administering to the subject an effective amount of a pharmaceutical composition comprised of a selective purine nucleoside analog and a pharmaceutically acceptable carrier. In one preferred embodiment, the disease is toxoplasmosis and the cells are a toxoplasma sp. In another preferred embodiment, the disease is a cancer or blood disorder and a parasitic gene(s) of purine salvage enzyme(s) has been introduced into the disease causing (e.g. malignant) mammalian cells. In a preferred embodiment, the parasitic genes for the purine salvage enzyme(s) is selected from the group consisting of adenosine kinase, purine nucleosidase (hydrolase or phosphorylase) or phosphoribosyltransferase genes.

In yet another aspect, the invention features combination therapies and pharmaceuticals for treating or preventing: i) a disease or condition in which the causative agent is a parasite, which is dependent on a parasite salvage pathway for its purine requirement and ii) a condition that renders a subject immunocompromised. In one embodiment, the method comprises co-administering to the subject, i) an effective amount of a purine nucleoside analog; and ii) an effective amount of an agent for treating or preventing the establishment or growth (systemic or local) of a cyst or infection. In a preferred embodiment, the method is for treating toxoplasmosis and AIDS and comprises administering to the subject, a combination drug comprising a purine nucleoside analog and an AIDS drug. In another embodiment, the method comprises co-administering to a subject, i) an effective amount of a purine nucleoside analog; and ii) an effective amount of an agent that suppresses the immune system (e.g. to permit allotransplantation).

The instant disclosed pharmaceutical compositions and methods of therapy exhibit high therapeutic indices, being highly toxic to disease causing cells, which are naturally or have been engineered to use the parasite salvage pathway enzymes for their purine requirement, but non-toxic to mammalian (host) cells. These compounds therefore represent safe and effective therapeutics for eliminating parasites in a subject's cells; or for eliminating other unwanted cells in a subject. The pharmaceutical compositions can be administered alone or in combination with other drugs.

Additional features and advantages of the invention will become more apparent from the following detailed description and claims.

DETAILED DESCRIPTION OF THE INVENTION

In contrast to their mammalian hosts, *T. gondii* are incapable of de novo purine synthesis and are totally dependent on the salvage pathways for their purine requirements (Schwartzman, J D and Pfefferkorn, E R, *Toxoplasma gondii*: Purine synthesis and salvage in mutant host cells and parasites. *Exptl Parisitol* 53: 77–86, 1982; Krug, E C, Marr, J J and R L Berens, Purine metabolism in *Toxoplasma gondii*: *J Biol Chem* 264: 10601–10607, 1989). In addition, *T. gondii* replicate rapidly and require large amounts of purines and pyrimidines for the synthesis of nucleic acids and other macromolecules. Indeed, the current standard treatment for *T. gondii* infections (antifolates and sulfonamides) uses this approach by blocking folate metabolism, thereby depriving the parasite of the necessary cofactors required for nucleotide biosynthesis (Luft, B J and Remington J S, Toxoplasmic encephalitis. *J Infect Dis* 157:1–6, 1988; McCabe, R. and Remington, J S, Toxoplasmosis: The time has come. *N. Engl. J. Med.* 318: 313–315, 1988). Enzymes involved with *T. gondii* nucleotide metabolism, therefore are potential targets for chemotherapeutic intervention.

The present invention is based on the finding that certain purine nucleoside analogs selectively interfere with enzymes involved in the purine salvage pathways of *Toxoplasma gondii*. The high activity of these enzymes and the unique characteristics of nucleotide metabolism in parasites makes these enzymes excellent targets for chemotherapy.

One of the significant enzymatic reactions in the purine salvage pathways in *T. gondii* is direct phosphorylation of adenosine to adenosine monophosphate (AMP), from which all other purine nucleotides can be synthesized (Krug E C, Marr J J and Berens R L, Purine metabolism in *Toxoplasma gondii J Biol Chem* 264: 10601–10607, 1989). The reaction is catalyzed by the enzyme adenosine kinase (EC 2.7.1.20), which is approximately 10-fold more active than any other purine salvage enzyme in these parasites (Krug E C, Marr J J and Berens R L, Purine metabolism in *Toxoplasma gondii. J Biol Chem* 264: 10601–10607, 1989). This contrasts sharply with mammalian cells where adenosine is predominantly deaminated to inosine, which is then cleaved to hypoxanthine by the sequential reactions of adenosine deaminase and purine nucleoside phosphorylase.

*T. gondii* Adenosine Kinase Binding

The binding of one hundred and thirty three purine nucleoside analogs were evaluated as potential ligands of *T. gondii* adenosine kinase as described in Example 1. Three types of purine nucleoside analogs were screened as follows: (1) analogs with either endocyclic or exocyclic substitutions on the purine moiety; (2) analogs with substitutions on the pentose moiety; and (3) analogs with substitutions on both the purine and pentose moieties.

Table 1 shows the effect of various substitutions at the different positions of adenosine on binding to *T. gondii* adenosine kinase as compared to that of the reference compound adenosine.

TABLE 1

Binding ($AppK_i$) values for inhibition of *T. gondii* adenosine kinase.

| | Compound | Source | $AppK_i(\mu M)^a$ |
|---|---|---|---|
| 1 | β-D-Adenosine (9-(β-D-ribofuranosyl)adenine) | SIG | 7.0 ± 3.3 |
| 2 | 2 β-L-Adenosine | RS | † |
| 3 | α-Adenosine (9-α-D-ribofuranosyl)adenine) | SIG | 8,400 ± 2,200 |
| | Modifications in the Purine Moiety | | |
| | 1-Position Substitutions | | |
| 4 | Adenosine-$N^1$-oxide | SIG | 1,230 ± 10 |
| 5 | 1-Deazaadenosine | BWC | † |
| 6 | 1-Methyladenosine | SIG | 88 ± 28 |
| | 2-Position Substitutions | | |
| 7 | 2-Chloroadenosine | SIG | 870 ± 50 |
| 8 | 2-Fluoroadenosine | SC | 3,000 ± 500 |
| 9 | 2-Phenylaminoadenosine | RBI | † |
| | 3-Position Substitutions | | |
| 10 | 3-Deazaadenosine | BWC | † |
| | 6-Position Substitutions | | |
| 11 | Purine riboside (Nebularine) | SIG | 170 ± 20 |
| 12 | 6-Bromopurine riboside | NCI | 28 ± 2 |
| 13 | 6-Chloropurine riboside | SIG | 9.5 ± 0.3 |
| 14 | 6-Iodopurine riboside | NCI | 18 ± 1 |
| 15 | 6-Oxopurine riboside (inosine) | SIG | † |
| 16 | 6-Methoxypurine riboside | SIG | 370 ± 40 |
| 17 | 6-Thiopurine riboside (6-mercaptopurine riboside) | SIG | 5,300 ± 400 |
| 18 | 6-Methylmercaptopurine riboside | SIG | 22 ± 1 |
| 19 | 6-Ethylmercaptopurine riboside | NCI | 330 ± 3 |
| 20 | 6-Benzylmercaptopurine riboside | NCI | 140 ± 10 |
| 21 | 6-(p-Nitrobenzyl)mercaptopurine riboside (NBMPR) | NCI | 140 ± 10 |
| 22 | 6-(7-Nitrobenzofuroxan-4-yl)mercaptopurine riboside | NCI | 11 ± 1 |
| 23 | 6-Selenopurine riboside | SIG | 130 ± 20 |
| 24 | 6-(p-Nitrobenzyl)selenopurine riboside | SIG | 84 ± 46 |
| | $N^6$-Position Substitutions | | |
| 25 | $N^6$-Hydroxyadenosine | SIG | 160 ± 30 |
| 26 | $N^6$-Methyladenosine | SIG | 23 ± 1 |
| 27 | $N^6$-Dimethyladenosine | SIG | 55 ± 6 |
| 28 | $N^6$-Ethyladenosine | BWC | 100 ± 3 |
| 29 | $N^6$-(2-Hydroxyethyl)adenosine | SIG | 320 ± 50 |
| 30 | $N^6$-Allyladenosine | BWC | 220 ± 20 |
| 31 | $N^6$-(Propynyl)adenosine | NCI | 150 ± 5 |
| 32 | $N^6$-(n-Butyl)adenosine | BWC | 220 ± 90 |
| 33 | $N^6$-(3-Chloro-2-butenyl)adenosine | NCI | 220 ± 9 |
| 34 | $N^6$-(4-Hydroxy-3-methyl-trans-2-butenyl)adenosine | SIG | 280 ± 20 |

TABLE 1-continued Binding (AppK$_i$) values for inhibition of *T. gondii* adenosine kinase.

| | Compound | Source | AppK$_i$($\mu$M)[a] |
|---|---|---|---|
| 35 | N$^6$-(n-Pentyl)adenosine | BWC | 140 ± 10 |
| 36 | N$^6$-(2-Isopentenyl)adenosine | SIG | 51 ± 4 |
| 37 | N$^6$-Cyclopentyladenosine | SIG | 350 ± 10 |
| 38 | N$^6$-Furfuryladenosine (kinetin riboside) | SIG | 180 ± 10 |
| 39 | N$^6$-(n-Hexyl)adenosine | BWC | 76 ± 4 |
| 40 | N$^6$-Cyclohexyladenosine | SIG | 240 ± 70 |
| 41 | N$^6$-(3,7-Dimethyl-2,6-octadienyl)adenosine | NCI | 100 ± 5 |
| 42 | N$^6$-(n-Decyl)adenosine | BWC | 380 ± 130 |
| 43 | N$^6$-Phenyladenosine | BWC | 88 ± 12 |
| 44 | N$^6$-Benzoyladenosine | SIG | 23 ± 1 |
| 45 | N$^6$-Benzyladenosine | SIG | 100 ± 30 |
| 46 | N$^6$-(p-Aminobenzyl)adenosine | SIG | 120 ± 10 |
| 47 | N$^6$-(p-Methoxybenzolyl)adenosine (N$^6$-anisoyladenosine) | SIG | 3.9 ± 0.9 |
| 48 | N$^6$-Phenylethyladenosine | BWC | 390 ± 240 |
| 49 | (R)-N$^6$-(2-Phenylisopropyl)adenosine | RBI | 750 ± 30 |
| 50 | (S)-N$^6$-(2-Phenylisopropyl)adenosine | RBI | 480 ± 70 |
| | 7-Position Substitutions | | |
| 51 | 7-Deazaadenosine (Tubercidin) | SIG | 340 ± 80 |
| 52 | 7-Chloro-7-deazaadenosine (5-Chlorotubercidin) | NCI | 10 ± 1 |
| 53 | 7-Iodo-7-deazaadenosine (5-Iodotubercidin) | RBI | 1.6 ± 0.1 |
| 54 | 7-Cyano-7-deazaadenosine (Toyocamycin) | NCI | 21 ± 2 |
| 55 | 7-Carboxamido-7-deazaadenosine (Sangivamycin) | NCI | 56 ± 4 |
| 56 | 7-Carboxyamidoxime-7-deazaadenosine | NCI | 200 ± 6 |
| | 8 Position Substitutions | | |
| 57 | 8-Azaadenosine | SIG | 23 ± 6 |
| 58 | 8-Azidoadenosine | JM | 520 ± 120 |
| 59 | 8-Bromoadenosine | SIG | 660 ± 70 |
| | 9-Position Substitutions | | |
| 60 | 9-Deazaadenosine | RK | 3,400 ± 1,300 |
| | 1,6-Position Substitutions | | |
| 61 | 1-Deazapurine riboside | BWC | † |
| 62 | 1,N$^6$-(Etheno)adenosine | SIG | 4,300 ± 900 |
| | 2,6-Position Substitutions | | |
| 63 | 2-Amino-6-chloropurine riboside | ALD | 1,800 ± 100 |
| 64 | 2-Amino-6-hydroxypurine riboside (guanosine) | SIG | † |
| 65 | (R)-2-Azido-N$^6$-(p-hydroxyphenylisopropyl)adenosine | ICN | 59 ± 5 |
| 66 | 2-Chloro-N$^6$-cyclopentyladenosine | RBI | 390 ± 90 |
| 67 | 2,6-Dihydroxypurine riboside (xanthosine) | SIG | † |
| | 6,7-Position Substitutions | | |
| 68 | 6-Chloro-7-deazapurine riboside | NCI | 72 ± 12 |
| 69 | 6-Hydrazino-7-deazapurine riboside | NCI | 180 ± 10 |
| 70 | N$^6$-Hydroxy-7-bromo-7-deazaadenosine | NCI | 37 ± 9 |
| 71 | N$^6$-Methyl-7-thiocarboxyamido-7-deazaadenosine | NCI | 150 ± 1 |
| | 7,8-Position Substitutions | | |
| 72 | 8-Aza-7-deazaadenosine | NCI | 1,700 ± 50 |
| 73 | 8-Bromo-7-carboxyamidoxime-7-deazaadenosine | NCI | 210 ± 30 |
| 74 | 8-Hydrazino-7-carboxamido-7-deazaadenosine (6-Hydrazinosangivamycin) | NCI | 160 ± 9 |
| | 6,7,8-Position Substitutions | | |
| 75 | 8-Aza-7-deazapurine riboside | BWC | 5,100 ± 400 |
| 76 | 8-Aza-6-ethylmercapto-7-deazapurine riboside | BWC | 210 ± 100 |
| 77 | 8-Aza-6-hydroxy-7-deazapurine riboside (allopurinol) | SIG | 15,000 ± 1,000 |
| 78 | 8-Aza-6-mercapto-7-deazapurine riboside | BWC | † |
| 79 | 8-Aza-6-methylmercapto-7-deazapurine riboside | BWC | 140 ± 30 |
| | Other Substitutions | | |
| 80 | 7-Carboxamido-7-deazaadenosine-N$^1$-oxide | NCI | 780 ± 70 |
| 81 | 8-Aza-9-deazaadenosine (formycin A) | SIG | 1,400 ± 200 |
| 82 | 8-Aza-9-deazainosine (formycin B) | SIG | 3,100 ± 200 |
| 83 | 8-Aza-6-methylmercaptopurine riboside | BWC | 130 ± 40 |
| 84 | Benzimidazole riboside ("1,3-dideazapurine riboside") | BWC | † |
| 85 | Coformycin | CAL | 2,000 ± 900 |

TABLE 1-continued

Binding (AppK$_i$) values for inhibition of *T. gondii* adenosine kinase.

| | Compound | Source | AppK$_i$($\mu$M)$^a$ |
|---|---|---|---|
| | *Modifications in the Pentose Moiety* | | |
| | 2'-Position Substitutions | | |
| 86 | Adenine arabinoside (ara-A) | SCH | 3,000 ± 700 |
| 87 | 2'-Deoxyadenosine | SIG | 4,200 ± 1,000 |
| 88 | 2'-O-Methyladenosine | SIG | † |
| 89 | 2'Tosyladenosine | SIG | † |
| | 3'-Position Substitutions | | |
| 90 | 3'-Deoxyadenosine (Cordycepin) | SIG | 1,100 ± 100 |
| 91 | 3'-O-Methyladenosine | SIG | † |
| 92 | Adenine xyloside | GG | 1,400 ± 100 |
| | 5'-Position Substitutions | | |
| 93 | 5'-Deoxyadenosine | SIG | 40 ± 3 |
| 94 | 5'-Amino-5'-deoxyadenosine | SIG | 220 ± 40 |
| 95 | 5'-Chloro-5'-deoxyadenosine | SIG | 210 ± 10 |
| 96 | 5'-Iodo-5'-deoxyadenosine | SIG | 230 ± 10 |
| 97 | 5'-Sufonyl adenosine (adenosine 5'-monosulfate) | SIG | 210 ± 60 |
| 98 | 5'-Methylthio-5'-deoxyadenosine | SIG | 530 ± 230 |
| 99 | adenosine 5'-Carboxylic acid (5'-Carboxyladenosine) | SIG | 1,100 ± 160 |
| 100 | 5'-Succinyladenosine (adenosine 5'-succinate) | SIG | 920 ± 600 |
| 101 | 5'-Isobutyl-5'-deoxyadenosine | SIG | 410 ± 90 |
| 102 | 5'-N-(Methyl)carboxamidoadenosine | RBI | † |
| 103 | 5'-N-(Ethyl)carboxamidoadenosine | RBI | † |
| 104 | 5'-N-(Cyclopropyl)carboxamidoadenosine | SIG | 1,100 ± 40 |
| 105 | 5'-(p-Fluorosulfonylbenzoyl)adenosine | FLU | 340 ± 40 |
| | Multiple Substitutions | | |
| 106 | 2',3'-Dideoxyadenosine | SIG | 5,500 ± 2,900 |
| 107 | Adenine lyxoside | NCI | 1,300 ± 70 |
| 108 | 2',3'-O-p-Anisylidene adenosine | SIG | 1,400 ± 200 |
| 109 | 2',3'-Di-O-acetyladenosine | SIG | † |
| 110 | 3',5'-Di-O-acetyladenosine | SIG | † |
| 111 | 4'-Flouro-5'-O-sulfamoyladenosine (nucleocidin) | AMC | 850 ± 220 |
| | Other Modifications | | |
| 112 | Carbocyclic adenosine | JM | 170 ± 30 |
| 113 | (±)-EHNA | SIG | † |
| 114 | Neplanocin A | NCI | 37 ± 10 |
| 115 | Adenine | SIG | 6,500 ± 2,600 |
| | *Modifications in the Purine and Pentose Moieties* | | |
| 116 | 1-Methyl-2'-deoxyadenosine | SIG | 8,000 ± 300 |
| 117 | N$^6$-Methyl-2'-deoxyadenosine | SIG | † |
| 118 | N$^6$-Benzoyl-2'-deoxyadenosine | FLU | 590 ± 20 |
| 119 | N$^6$-Dimethyl-3'-amino-3'-deoxyadenosine | SIG | 540 ± 80 |
| 120 | 7-Deaza-7-carboxamido-3'-deoxyadenosine (3'-Deoxysangivamycin) | LT | 110 ± 20 |
| 121 | 2'-Fluoro-2'-deoxyguanosine | SIG | † |
| 122 | 2',3'-O-Isopropylidene-6-mercaptopurine riboside | SIG | 3,900 ± 500 |
| 123 | 5'-Aminoimidazole-4-carboxamide riboside | SIG | 2,400 ± 200 |
| 124 | 3'(α-Amino-p-methoxyhydrocinnamamido)-3'-deoxy-N$^6$-dimethyladenosine (Puromycin) | SIG | 1,300 ± 300 |
| 125 | 4-(3-Hydroxymethyl-4,5-dihydroxy-2-cyclopenten-1-yl)amino-5-nitro-6-aminopyrimidine | VM | † |
| 126 | 4-(3-Hydroxymethyl-4,5-dihydroxy-2-cyclopenten-1-yl)amino-1,6-dihydro-5-nitro-6-oxopyrimidine | VM | † |
| 127 | 2-Amino-4-(3-hydroxymethyl-4,5-dihydroxy-2-cyclopenten-1-yl)aminto-1,6-dihydro-5-nitro-6-oxopyrimidine | VM | 940 ± 110 |

$^a$Apparent K$_i$ values ± the range were obtained from at least two separate estimations.
$^b$† = less than 10% inhibition at a concentration of 1 mM.

Overall, the best ligands to bind to adenosine kinase from *T. gondii* were adenosine analogs with 6-position substitutions. Two 6-substituted compounds, N$^6$-(p-methoxybenzoyl) adenosine and 6-chloropurine riboside, were found to bind strongly to the enzyme with appK$_i$ values of 3.9 and 9.5 $\mu$M, respectively.

Based on the inhibition data, a structure activity relationship for the binding of these analogs to the enzyme was formulated, using adenosine as a reference compound. It was concluded that the N1, N3, N7 and N9 of the purine ring are all required for binding of *T. gondii* adenosine kinase; whereas, the C8 carbon can be replaced with a nitrogen with only a slight reduction in binding (3-fold). In general, exocyclic substitutions at the 1-, 2- or 8-position diminished binding. At the 6-position, hydrophobic substitutions were preferred over hydrophilic substitutions; however, most exocyclic substitutions diminished binding.

In addition, there appears to be a "pocket" in the catalytic site of *T. gondii* adenosine kinase, adjacent to the 6-position, which is large enough to accomodate a substituted phenyl group. Two 7- substituted adenosine analogs, sangivanycin and toyocamycin, were found to bind with relatively good affinity (i.e. appKi<60 μM). The presence of 2'-hydroxyl group in the ribo configuration appears to be critical for binding to the enzyme, as removal of this group from sangivamycin (3'-deoxysangivamycin) reduced binding by only 2-fold. The presence of the 5'-hydroxyl group, which is considered essential if the ligand is to become a substrate, seems not essential for binding, as its removal diminished binding by only 6-fold. However, substitution of the 5'-hydroxyl group with hydrophilic or hydrophobic groups decreased binding significantly.

The following Table 2 summarizes the structure-activity relationship for the binding of purine nucleoside analog ligands to *T. gondii* adenosine kinase.

TABLE 2

Structure-activity relationship for the binding of nucleoside ligands to *T. gondii* adenosine kinase

| Position | Substituent Effect (numbers are with reference to the nucleoside analogs shown in Table 1) |
|---|---|
| 1-Position | Endocyclic "pyridine-type" nitrogen required; replacement with endocyclic methine group (1-deazaadenosine, 5) abolishes binding. |
| 2-Position | Exocyclic hydrogen required; substitution (e.g. chloro, 7; fluoro, 8; or amino, 63) significantly decreases (120 to 430-fold) or abolishes (e.g. phenylamino, 9) binding. |
| 3-Position | Endocyclic "pyridine-type" nirogen required; replacement with endocyclic methine group (3-deazaadenosine, 10) abolishes binding. |
| 6-Position | Exocyclic amino group preferred; elimination of group (purine riboside, 11) decreases binding (25-fold). Exocyclic substituents in lactim tautomeric form strongly preferred; substitution of amino group with groups in lactim tautomeric form (e.g. bromo, 12; chloro, 13; or iodo, 14) diminishes binding slightly (1.4- to 4-fold); substitution of amino group with groups in lactam tautomeric form (e.g. oxo 15; thio, 17; or seleno, 23) decreases (19- to 750-fold) or abolishes binding. |
| $N^6$-Position | Hydrophobic substituents preferred over hydrophilic substituents, e.g. ethyl (28) vs. 2-hydroxyethyl (29); straight chain aliphatic substituents preferred over cyclic aliphatic substituents, e.g. n-pentyl (35) vs. cyclopentyl (37); unsaturated substituents preferred over saturated substituents, e.g. 2-isopentenyl (36) vs. n-pentyl (35); aromtaic substituents preferred over non-aromatic substituents, e.g. phenyl (43) vs. cyclohexyl (40). Hydrophilic linkages (e.g. carbonyl, 49) between aromatic groups and $N^6$ preferred over hydrophobic linkages (e.g. methylene, 44). |
| 7-Position | Endocyclic "pyridine-type" nitrogen strongly preferred; replacement with endocyclic methine group (7-deazaadenosine, 51) decreases binding (49-fold). Hydrophobic exocyclic substituents (e.g. chloro, 52; or iodo, 53) attached to endocyclic carbon preferred over hydrophilic substituents (e.g. cyano, 54; carboximido, 55; or carbox amidoxime, 56). |
| 8-Position | Endocyclic methine group preferred but not required; replacement with endocyclic nitrogen (8-azaadenosine, 57) decreases binding slightly (3-fold). |
| 9-Position | Endocyclic nitrogen required; replacement with endocyclic carbon (9-deazaadenosine, 60) decreases binding significantly (490-fold). |
| 2'-Position | Exocyclic 2'-hydroxyl group in ribo configuration required for binding; elimination (2'-deoxyadenosine, 87) or substitution of group (e.g. methoxy, 88) significantly decreases (600-fold) or abolishes binding; change in configuration of group to ara configuration (86) significantly decreases binding (430-fold). |
| 3'-position | Exocyclic 3'-hydroxyl group in ribo configuration strongly preferred for binding; elimination (3'-deoxyadenosine, 91) or substitution of group (e.g. methoxy, 92) significantly decreases (150-fold) or abolishes binding; change in configuration of grup to xylo configuration (90) significantly decreases binding (200-fold). |
| 5'-Position | Hydroxymethyl or methyl group strongly preferred for binding; elimination of hydroxyl group (5'-deoxyadenosine, 93) decreases binding slightly (5.7-fold); substitution of hydroxyl group (with variety of groups, e.e. 94–106) significantly decreases (at least 30-fold) or abolishes binding. |
| Other | A pentose or "pentose-like" moiety in a ribo configuration required for binding; elimination (i.e. adenine, 116) of pentose moiety or a change to lyxo configuration (adenine lyxoside, 107) significantly decreases binding (930- and 190-fold, respectively); replacement of pentose moiety with hydroxylated cyclopentene moiety (neplanocin A, 114) decreases binding slightly (5.3-fold). β-D-nucleoside configuration required; change in configuration to α-D-nucleoside (α-D-adenosine, 3) significantly decreases binding (1200-fold); change in configuration to β-L-nucleoside (β-L-adenosine, 2) |

TABLE 2-continued

Structure-activity relationship for the binding of nucleoside ligands
to *T. gondii* adenosine kinase

| Position | Substituent Effect (numbers are with reference to the nucleoside analogs shown in Table 1) |
|---|---|
| | abolishes binding<br>Anti confomation around N-glycosidic bond preferred; change to syn confirmation (e.g. 8-bromoadenosine, 59) deceases binding (94-fold). |

Particularly preferred ligands of parasite adenosine kinase include substituted or unsubstituted D and L enantiomers, α- and β-anomers of: 6-[4-nitrobenzyl thio]-9-β-D-ribofuranosyl purine (NBMPR), 6-[4-nitrobenzyl thio]-9-β-D-ribofuranosyl purine 5'-monophosphate (NBMPR-P), 6-chloropurine riboside, 3'-deoxysangivamycin, $N^6$-(p-methoxybenzoyl)adenosine, nitrobenzyl-6-selenoriboside, $N^6$-benzyladenosine, $N^6$-azidobenzyladenosine and $N^6$-nitrobenzyladenosine.

The metabolism and fate of 6-substituted 9-β-D-ribofuranosylpurines (NBMPR or its nucleotide analog NBMPR-P) were studied as described in Example 3. NBMPR or its nucleotide analog NBMPR-P were found to kill *T. gondii* grown in human fibroblasts in a dose dependent manner without apparent toxicity to host cells. Doses up to 100 μM did not affect host cells.

Another significant enzymatic reactions in the *T. gondii* purine salvage pathway is the conversion of purines, e.g. adenine, guanine, hypoxanthine and xanthine, to their respective nucleoside 5'-monophosphates by phosphoribosyltransferase activities (Schwartzman, J D and Pfefferkorn, E R, *Toxoplasma gondii*: Purine synthesis and salvage in mutant host cells and parasites. *Exptl Parisitol* 53: 77–86, 1982; Krug, E C, Marr, J J and R L Berens, Purine metabolism in *Toxoplasma gondii*: *J. Biol Chem* 264: 10601–10607, 1989; Pfefferkorn E R and Pfefferkorn L C, *Toxoplasma gondii*: Specific labeling of nucleic acids of intracellular parasites in Lesch-Nyhan cells. *Exptl. Parasitol.* 41: 95–104, 1977; and O'Sullivan W J, Johnson A M, Finney K G, Gero A M, Hagon E, Holland J W amd Smithers G W. Pyrimidine and purine enzymes in *Toxoplasma gondii*. *Aust J Exptl Biol Med Sci* 59:763–767, 1981). In addition to the nucleobases, inosine and guanosine are first cleaved by purine nucleosidase (hydrolase or phosphorylase) to hypoxanthine and guanine, respectively, and then converted to nucleotides by the phosphoribosyltransferase activities. Purine nucleosidase (phosphorylase or hydrolases) converts a purine nucleoside to a purine, which can be sequentially phosphorylated by a phosphoribosyltransferase activity.

Kinetic parameters of *T. gondii* phosphoribosyltransferases using hypoxanthine, guanine, xanthine or adenine as substrates were determined as described in Example 2. Hypoxanthine showed an apparent $K_m$ of 1.2±0.1 mM and an apparent $V_{max}$ of 0.94±0.01 mmol/min per mg protein. Guanine showed an apparent $K_m$ of 1.3±0.4 mM and an apparent $V_{max}$ of 0.72±0.07 mmol/min per mg protein. Xanthine showed an apparent $K_m$ of 3.0±0.4 mM and an apparent $V_{max}$ of 1.1±0.1 mmol/min per mg protein. Adenine exhibited an apparent $K_m$ of 2.9±0.8 mM and an apparent $V_{max}$ of 0.099±0.007 mmol/min per mg protein. The efficiencies of these activities (i.e. $V_{max}/K_m$) were found to be in the order hypoxanthine>guanine>xanthine>adenine. This ranking differs from a previously reported order of specific activities which was xanthine>hypoxanthine>guanine>adenine (Krug E C, Marr J J and R L Berens, Purine metabolism in *Toxoplasma gondii* *J. Biol. Chem.* 264: 1061–10607, 1989).

The pH optima for *T. gondii* phosphoribosyltransferase activity using hypoxanthine (HPRTase), guanine (GPRTase), xanthine (XPRTase) or adenine (APRTase) as substrates were found to be 7.5, 7.5, 7.8 and 8.0–9.5 respectively. Thus, the order of efficiencies for these substrates may at least partially reflect the difference between the pH employed (i.e. 7.4) and the pH optima for the different substrates. Competition studies between the four substrates for *T. gondii* phosphoribosyltransferase activity were conducted in order to ascertain how many separate enzyme activities are present in these parasites. Adenine did not inhibit either GPRTase or XPRTase. Both hypoxanthine and xanthine were competitive inhibitors of GPRTase; whereas, hypoxanthine was a noncompetitive inhibitor of XPRTase and guanine was a competitive inhibitor. These results indicate that at least two phosphoribosyltransferases are present in *T. gondii*. One enzyme uses hypoxanthine, guanine and xanthine as substrates, while the other enzyme uses only adenine. However, the noncompetitive inhibition demonstrated by hypoxanthine towards XPRTase, suggests that there may be a third enzyme which uses xanthine.

Sixty-eight compounds, mostly purine analogs, were evaluated as ligands of *T. gondii* XPRTase and GPRTase by examining their ability to inhibit these reactions in vitro. The purine nucleobase analogues that were screened included those having ring modifications (e.g. aza and deaza analogs) and/or exocyclic substitutions at various positions. Inhibition was quantified by determining apparent $K_i$ values for compounds that inhibited these activities by greater than 10% at a concentration of 0.9 mM. The mean and range of the apparent Ki values for these compounds, determined from at least three separate estimations of the apparent $K_i$s are presented in Table 3.

TABLE 3

Apparent $K_i$ values for inhibition of *T. gondii* XPRTase and GPRTase

| | Compound | Source | Apparent $K_i$ (mM)‡ | |
|---|---|---|---|---|
| | | | XPRTase | GPRTase |
| 1 | Hypoxanthine(6-oxopurine) | SIG | 3.5 ± 0.3 | 1.1 ± 0.1 |
| | 2-Position substitutions | | | |
| 2 | 2-Aminohypoxanthine (guanine) | SIG | 12 ± 2 | 10 ± 2 |
| 3 | 2-Methylaminohypoxanthine ($N^2$-methylguanine) | SIG | † | † |
| 4 | 2-Oxohypoxanthine (xanthine) | SIG | 14 ± 2 | 16 ± 4 |
| 5 | 2-Thiohypoxanthine (2-thioxanthine or 6-oxo-2-thiopurine) | SIG | 68 ± 18 | 66 ± 11 |
| | 6-Position substitutions | | | |
| 6 | Purine | CDC | † | † |
| 7 | 6-Aminopurine (adenine) | SIG | † | † |
| 8 | 6-Methylaminopurine (($N^6$-methyladenine) | SIG | 970 ± 170 | 770 ± 280 |
| 9 | 6-Benzylaminopurine ($N^6$-benzyladenine) | SIG | 1100 ± 300 | 1400 ± 600 |
| 10 | 6-Methoxypurine | CDC | 380 ± 90 | 400 ± 80 |
| 11 | 6-Thiopurine (purine-6-thione) | CDC | 6 ± 1 | 15 ± 1 |
| 12 | 6-Chloropurine | CDC | 100 ± 30 | 48 ± 3 |
| 13 | 6-Iodopurine | CDC | † | † |
| 14 | 6-Methylpurine | CDC | † | 1100 ± 500 |
| | 8-Position substitutions | | | |
| 15 | 8-Azahypoxanthine (8-aza-6-oxopurine) | CDC | 2000 ± 500 | 610 ± 190 |
| 16 | 8-Oxohypoxanthine (6,8-dioxopurine) | CDC | 4100 ± 1000 | † |
| 17 | 8-Thiohypoxanthine (6-oxopurine-8-thione) | CDC | 420 ± 100 | 500 ± 150 |
| | 1,2-Position substitutions | | | |
| 18 | 2-Amino-1-methylhypoxanthine (1-methylguanine) | SIG | 40 ± 5 | 150 ± 30 |
| 19 | 2-Oxo-1-methylhypoxanthine (1-methylxanthine) | FLU | 1400 ± 400 | 3700 ± 400 |
| | 2,6-Position substitutions | | | |
| 20 | 2-Aminopurine | CDC | 67 ± 32 | 280 ± 96 |
| 21 | 2-Oxopurine (2-hydroxypurine) | SIG | 570 ± 120 | 430 ± 110 |
| 22 | 2,6-Diaminopurine (2-aminoadenine) | CDC | 880 ± 280 | 460 ± 210 |
| 23 | 6-Amino-2-oxopurine (isoguanine) | NBC | 53 ± 15 | 220 ± 60 |
| 24 | 6-Amino-2-chloropurine (2-chloroadenine) | CDC | 2200 ± 900 | 630 ± 180 |
| 25 | 6-Amino-2-methylpurine (2-methyladenine) | SIG | 370 ± 110 | 2500 ± 800 |
| 26 | 2-Aminopurine-6-thione (6-thioguanine) | SIG | 22 ± 12 | 6 ± 0.3 |
| 27 | 2,6-Dithionepurine (dithioxanthine) | CDC | 420 ± 80 | 300 ± 30 |
| 28 | 2-Oxo-6-thiopurine (6-thioxanthine) | SIG | 246 ± 82 | 318 ± 128 |
| 29 | 2-Amino-6-chloropurine | CDC | 230 ± 50 | 890 ± 170 |
| 30 | 2,6-Dichloropurine | CDC | 410 ± 80 | 3000 ± 1600 |
| | 2,7-Position substitutions | | | |
| 31 | 2-Amino-7-deazahypoxanthine (7-deazaguanine) | SIG | 26 ± 5 | 93 ± 6 |
| 32 | 2-Amino-7-methylhypoxanthine (7-methylguanine) | SIG | 3100 ± 1500 | 3200 ± 2000 |
| 33 | 2-Oxo-7-methylhypoxanthine (7-methylxanthine) | CDC | 1900 ± 400 | 5700 ± 2300 |
| | 2,8-Position substitutions | | | |
| 34 | 2-Amino-8-azahypoxanthine (8-azaguanine) | CDC | 2600 ± 1000 | 450 ± 90 |
| 35 | 2-Amino-8-bromohypoxanthine (8-bromoguanine) | SIG | 540 ± 120 | 1600 ± 400 |
| 36 | 8-Aza-2-oxohypoxanthine (8-azaxanthine) | CDC | † | † |
| | 6,8-Position substitutions | | | |
| 37 | 8-Aza-6-aminopurine (8-azaadenine) | SIG | 3500 ± 1400 | 1800 ± 800 |
| 38 | 6-Amino-8-bromopurine (8-bromoadenine) | CDC | 750 ± 1000 | 630 ± 140 |
| | 6,9-Position substitutions | | | |
| 39 | 6-Amino-9-ethylpurine (9-ethyladenine) | CDC | † | 1000 ± 400 |
| 40 | 6-Amino-9-cyclohexylpurine (9-cyclohexyladenine) | CDC | † | 3200 ± 800 |
| | Other Di-Substitutions | | | |
| 41 | 6-Amino-1-methylpurine (1-methyladenine) | CDC | 310 ± 90 | 5900 ± 3000 |
| 42 | 2-Oxohypoxanthine-$N^3$-oxide (xanthine-$N^3$-oxide) | SIG | 1300 ± 300 | 5500 ± 1200 |
| 43 | 2-Oxo-3-methylhypoxanthine (3-methylxanthine) | FLU | † | † |
| 44 | 2-Amino-9-methylhypoxanthine (9-methylguanine) | CDC | 230 ± 50 | 610 ± 150 |
| 45 | 8-Aza-7-deazahypoxanthine (allopurinol) | SIG | 35 ± 6 | 130 ± 20 |

TABLE 3-continued

Apparent $K_i$ values for inhibition of *T. gondii* XPRTase and GPRTase

| | | | Apparent $K_i$ (mM)‡ | |
|---|---|---|---|---|
| | Compound | Source | XPRTase | GPRTase |
| | Multiple substitutions | | | |
| 46 | 2-Amino-1-methylpurine | SIG | 290 ± 90 | 730 ± 180 |
| 47 | 2,6-Dioxo-3-isobutyl-1-methylpurine | SIG | 1500 ± 600 | † |
| 48 | 6-Amino-7-deazapurine (7-deazaadenine) | BWC | 1700 ± 500 | 5800 ± 900 |
| 49 | 8-Aza-6-oxo-1,3-dimethylpurine | SHC | † | † |
| 50 | 1,2,4-Triazolo(1,5,-a)pyrimidine (1-deaza-5-azapurine) | ALD | † | † |
| 51 | 8-Aza-2,6-diaminopurine (8-aza-2-aminoadenine) | SIG | 850 ± 230 | 1300 ± 400 |
| 52 | 8-Aza-7-deaza-6-aminopurine (8-aza-7-deazaadenine) | CDC | 81 ± 52 | † |
| 53 | 8-Aza-7-deaza-6-thiopurine | BWC | 880 ± 330 | 970 ± 120 |
| 54 | 8-Aza-1,3-dideazapurine (benzotriazole) | CDC | 5200 ± 2300 | † |
| 55 | 8-Aza-1-nitro-1,3-dideazapurine (5-nitrobenzotriazole) | ALD | 390 ± 430 | † |
| 56 | 2,6-Dioxo-7-(b-hyydroxypropyl)-1,3-dimethylpurine | SIG | 1900 ± 1200 | † |
| 57 | 2,6-Dioxo-1,3,7-trimethylpurine (caffeine) | SIG | 1000 ± 400 | 840 ± 280 |
| 58 | 2,6-Dioxo-1,3,9-trimethylpurine (isocaffine) | FLU | 5300 ± 1300 | 6100 ± 2400 |
| 59 | 3-Methyl-2,6,8-trioxopurine | FLU | † | † |
| 60 | 1,3-Dimethyl-2,6,8-trioxopurine | FLU | † | † |
| | Other substitutions | | | |
| 61 | Benzonitrile | CDC | 870 ± 290 | 580 ± 170 |
| 62 | 1,3-Dimethylpteridine | SHC | † | † |
| 63 | 6-Hydroxymethylpterin | SIG | 3400 ± 1800 | 6600 ± 4500 |
| 64 | Cytosine (4-amino-2-oxopyrimidine) | SIG | 286 ± 60 | 476 ± 90 |
| 65 | 5-Fluorocytosine | CDC | 657 ± 180 | 431 ± 100 |
| 66 | Isocytosine (2-amino-4-oxopyrimidine) | NBC | 1060 ± 270 | 616 ± 200 |
| 67 | Uracil (2,4-dioxopyrimidine) | SIG | 808 ± 20 | 699 ± 140 |
| 68 | 4-Oxopyrimidine (4-hydroxypyrimidine) | CDC | 379 ± 100 | 445 ± 130 |

‡Apparent $K_i$ values ± range were obtained from at least three separate estimations of the apparent $K_i$.
†Less than 10% inhibition at a concentration of 0.9 mM.

A structure-activity relationship for the binding of ligands to *T. gondii* XPRTase and GPRTase was formulated using hypoxanthine (6-oxopurine) as a reference compound. Structural features of purine analogues required or strongly preferred for binding to both activities is detailed in Table 4.

TABLE 4

Structure-activity relationship for the binding of nucleobase ligands to *T. gondii* XPRTase and GPRTase

| Position | Substituent Effect |
|---|---|
| 1-Position | A pyrrole-type nitrogen strongly preferred or required for binding; substitution of exocyclic methyl group (e.g. 1-methylguanine, 18; or 1-methylxanthine, 19) decreases binding. |
| 2-Position | Exocyclic substitutions to purine (6) (e.g. oxo, 21; or amino, 20) generally increase binding; exocyclic substitutions to other compounds. (e.g. hypoxanthine, 1) usually decrease (e.g. amino, 2; oxo, 4; or thio, 5) or abolish (e.g. methylamino, 3) binding. |
| 3-Position | Exocyclic substituents decrease (e.g. oxide, 42) or abolish (e.g. methyl, 42) binding. |
| 6-Position | Exocyclic oxo or thioxo group in the lactam tautomeric form is required for binding; substitution of 6-position oxo group of hypoxanthine (1) with thio group (6-thiopurine, 11) decreases binding slightly (1.7- and 14-fold‡, respectively); elimination (i.e. purine, 6) or substitution of the 6-position oxo group decreases (e.g. amino, 7; methylamino, 8; benzylamino, 9; or chloro, 12) or abolishes (e.g. iodo, 13 or methyl, 14) binding. |
| 7-Position | A pyridine-type nitrogen is preferred for binding; replacement with methine group (e.g. 7-deazaguanine, 31) decreases binding slightly (2.2.- and 9.3-fold‡, respectively). Substitution of exocyclic methyl group (e.g. 7-methylguanine, 32; or 7-methylxanthine, 33) decreases binding by at least 136-fold. |
| 8-Position | Endocyclic methine group required for binding; replacement with nitrogen significantly decreases (e.g. 8-azahypoxanthine 15; or 8- |

TABLE 4-continued

Structure-activity relationship for the binding of nucleobase ligands to
*T. gondii* XPRTase and GPRTase

| Position | Substituent Effect |
|---|---|
| | azaguanine, 34) or abolishes (8-azaxanthine, 36) binding. Exocyclic substituents (e.g. oxo, 16; thio, 17; or bromo, 35) significantly decrease (at least 120-fold) or abolish binding. |
| 9-Position | Substitution of exocyclic methyl group (e.g. 9-methylguanine, 44) decreases binding (19- and 61-fold‡, respectively). |

‡Refers to XPRTase and GPRTase, respectively.

Based on the structure activity relationship studies described above, purine nucleoside analogs that are ligands of a parasite salvage pathway enzyme comprise D (+) or L (−) enantiomers, α or β anomers of the following structural formula:

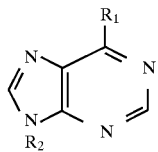

wherein, $R_1$ is a halogen, $OR_6$, $SR_6$, $SeR_6$ or $CH_2R_6$ and $R_6$ is alkyl, alkene, arylalkyl, or aryl;

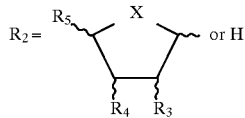

X is $CH_2$, O or S;

$R_3$ is H, OH, or a halogen;

$R_4$ is H, OH, or a halogen; and $R_5$ is $CH_3$, $CF_3$, $CH_2OH$, or $CH_2OY$ and Y is a carbon ester or phosphorus.

The alkyl, alkene, arylalkyl and aryl groups (hereinafter hydrocarbon groups) comprising $R_6$ can be either straight or branched chains, saturated or unsaturated. Unsaturated groups may have a single site of unsaturation or a plurality of unsaturated sites. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynyl, ethynylene, propyl, propylene, propenyl, propenylene, propynyl, and propynylene. Examples of higher hydrocarbon groups (from four to about ten carbons) include butyl, t-butyl, butenyl, butenylene, and butynyl, butynylene, nonyl, nonylene, nonenyl, nonenylene, nonynyl, and nonynylene.

The alkyl or alkylene groups may be substituted with one or more oxygen or halogen atom to form alkoxy, haloalkyl, alkoxyene, and haloalkylene groups. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodine. Examples of substituted hydrocarbon groups which are useful within this invention are similar to hydrocarbon groups set forth above except for the incorporation of oxygen(s) or halogen(s) into the groups.

Purines and a number of purine analogs are available from commercial sources (Tables 1 and 3). Alternatively, a particular purine analog can be made from the corresponding purine or a purine analog using standard chemical procedures.

Once prepared, candidate purine analogs can be screened for ability to bind to parasitic adenosine kinase, nucleosidase (hydrolase or phosphorylase), and/or parasitic phosphoribosyltransferase, for example as described in Examples 1 and 2. Alternatively, the efficacy by which a particular compound can prevent (e.g. inhibit growth) or treat (e.g. decrease the number and/or size of a parasite) can be tested in the human fibroblast assay described in Example 3.

Appropriate compounds, as well as combinations of compounds, can be prepared as pharmaceutical compositions upon admixture with a pharmaceutically acceptable carrier. Examples of such carriers include solutions (e.g. saline), solvents, dispersion media, delay agents, emulsions and the like. The identity and use of such media for pharmaceutically active substances are well known in the art.

Pharmaceutical compositions comprising purine analogs can then be administered to a subject for treatment of a disease, which is caused by or contributed to by parasites, which are dependent on salvage pathway enzymes for their purine requirement. Examples of such parasites are *Toxoplasma gondii, Entamoeba histolytica, Eimeria tenella, Leishmania donovani, Plasmodium falciparum, Tritichomonas foetus* and *Trypanosoma cruzi*. In order to treat a disease caused by such a parasite in a subject, an effective amount of a purine analog is administered to the subject. In addition, administration of an effective amount of a purine analog to a pregnant woman can prevent or decrease the transmission of a parasitic infection from the mother to her unborn child.

For use in therapy, an effective amount of a purine nucleoside analog can be administered to a subject (e.g. a human or other mammal) by any mode, which allows the small molecule to be in contact with the parasite or transfected mammalian cell. Preferred routes of administration include oral and transdermal (e.g. via a patch). Examples of other routes of administration include injection (subcutaneous, intravenous, parenteral, intraperitoneal, intrathecal, etc.). The injection can be in a bolus or a continuous infusion. Depending on the route of administration, the purine nucleoside analog can be associated with or disposed in a selected material to protect it from natural conditions which may detrimentally affect its ability to perform its intended function, increase its in vivo availability or increase its uptake by a specific organ (e.g. the central nervous system to treat toxoplasma induced encephalitis).

An "effective amount" of a purine nucleoside analog refers to that amount necessary or sufficient to prevent, reduce or eliminate the symptoms of the parasitic infection. The effective amount can vary depending on such factors as the particular parasite or extent of infection, the particular adenosine analog being administered or the size of the subject. Doses of NBMPR or NBMPR-P of up to about 100 µM were found to effectively eliminate *T. gondii* parasites without affecting mammalian cells. One of ordinary skill in the art can empirically determine the effective amount of a particular purine analog which is administered alone or in conjunction with another active agent, without necessitating undue experimentation.

The purine nucleoside-like, small molecule drugs disclosed herein can be administered alone or in conjunction with another active agent as a combination therapy. For example, since the initiation of a parasitic infection or the onset of symptoms can be triggered or enhanced when a subject is in an immunocompromised condition (e.g. from infection, cancer, stress etc.), an appropriate active agent for co-administration with a purine nucleoside analog can be an agent for treating or preventing the establishment or growth (systemic or local) of a tumor or infection. Examples of such agents include drugs (e.g. antibiotics, anti-virals, antifungals, anti-protozoals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense), chemotherapeutic nucleotides, peptides, non-specific (non-antibody) proteins (e.g. sugar oligomers), boron containing compounds (e.g. carborane), photodynamic agents (e.g. rhodamine 123) and enediynes (e.g. calicheamicins, esperamicins, dynemicin, neocarzinostatin chromophore, and kedarcidin chromophore). As a combination therapy, a purine nucleoside analog can be administered prior to, simultaneously or after the administration of the other active agent.

In a preferred embodiment for treating or preventing the establishment or growth of a tumor and a disease or condition which is caused by or contributed to by a parasite which is dependent on a salvage pathway for its purine requirement, the combination therapeutic compound can comprise a purine nucleoside analog; a radionuclide, toxin, hormone antagonist, heavy metal complex, oligonucleotide, chemotherapeutic nucleotide, peptide, non-specific (non-antibody) protein, boron compound or an enediyne; and a pharmaceutically acceptable carrier.

In a preferred embodiment for treating or preventing the establishment or growth of a bacterial infection and a disease or condition which is caused by or contributed to by a parasite which is dependent on a salvage pathway for its purine requirement, the therapeutic compound can comprise a purine nucleoside analog; an antibiotic, radionuclide or oligonucleotide; and a pharmaceutically acceptable carrier.

In a preferred embodiment for treating or preventing the establishment or growth of a viral infection and a disease or condition which is caused by or contributed to by a parasite which is dependent on a salvage pathway for its purine requirement, the therapeutic compound can comprise a purine nucleoside analog; an antiviral compound, radionuclide or oligonucleotide; and a pharmaceutically acceptable carrier. In a particularly preferred embodiment, the viral infection is by the Human Immunodeficiency Virus (HIV) and the antiviral is selected from the group consisting of: 3'-azido-2',3'-dideoxythymidine (AZT), 2',3'-dideoxycytidine (ddC), 2',3'-didehydro-2',3'-dideoxythymidine (d4T), 3'-thia-2',3'-dideoxycytidine (3TC),2',3'-dideoxyinosine (ddI),2',3'-dideoxyguanosine (ddG), or 2'-β-fluoro-2',3'-dideoxyadenosine (F-ara-ddA), can be administered to a subject.

In a preferred embodiment for treating or preventing the establishment or growth of a fungal infection, and a disease or condition which is caused by or contributed to by a parasite which can metabolize adenosine, the therapeutic compound can comprise a purine nucleoside analog; an antifungal compound, radionuclide or oligonucleotide; and a pharmaceutically acceptable carrier.

In another embodiment, appropriate active agents for co-administration can be agents that suppress the immune system, for example to permit allotransplantation. Examples of suitable immunosuppressive agents to be co-administered with a purine nucleoside analog include: cyclosporine, azathioprine, methotrexate, immunoglobulin preparations (e.g. Rhogam, Gamulin), adrenocorticosteroids, sulfasalazine, FK-506, methoxsalen, rapamycin and thalidomide.

In another embodiment, the disease is a cancer or blood disorder and a parasitic gene(s) of purine salvage enzyme(s) has been introduced into the disease causing (e.g. malignant) cells. In a preferred embodiment, the parasitic genes for purine salvage enzymes are selected from the group consisting of adenosine kinase, purine nucleosidase (nucleoside hydrolase or phosphorylase) or a phosphoribosyltransferase.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Structure-Activity Relationship of the Binding of Nucleoside Ligands to Adenosine Kinase from *Toxoplasma Gondii*

Chemicals and supplies. The source of the compounds screened as inhibitors of adenosine kinase are indicated in Table 1 by the following abbreviations: ALD, Aldrich Chemical Co., Inc., Milwaukee, Wis.; AMC, American Cyanamid Co., Lederle Laboratories, Pearl River, N.Y.; BW, Burroughs Wellcome Co., Research Triangle Park, N.C.; CAL, Calbiochem, San Diego, Calif.; FLU, Fluka Chemical Co., Ronkonkoma, N.Y.; ICN, ICN Biomedicals, Inc., Costa Mesa, Calif.; GG, Dr. Gilles Gosselin, Université de Montpellier, Montpellier, France; AM, Dr. John A. Montgomery, Southern Research Institute, Birmingham, Ala.; LBT, Dr. Leroy B. Townsend, University of Michigan, Ann Arbor, Mich.; NCI, Drug Synthesis and Chemistry Branch, Developmental Therapeutic Program, Division of Cancer Treatment, National Cancer Institute, Bethesda, Md.; RSK, Dr. Robert S. Klein, Montefiore Medical Center, Bronx, N.Y.; SCH, Schweizerhall, Inc., Piscataway, N.J.; SHC, Dr. Shih Hsi Chu, Brown University, Providence, R.I.; SIG, Sigma Chemical Co., St. Louis, Mo.; VEM, Dr. Victor E. Marquez, National Cancer Institute, Bethesda, Md. [8-$^{14}$C]Adenosine (45 mCi/mmol), [G-$^{13}$H]NBMPR (36 Ci/mmol), and [5,6-$^{13}$H]uracil (38 Ci/mmol) were purchased from Moravek Biochemicals, Brea, Calif.; Scintilene scintillation fluid was from Fisher Scientific, Pittsburgh, Pa.; silica gel G/UV$_{254}$ Polygram thin layer chromatography plates were from Brinkmann, Westbury, N.Y.; and Bio-Rad protein assay kits were from Bio-Rad Laboratories, Richmond, Calif. (+)-erythro-9-(2-S-hydroxy-3-R-nonyl) adenine (EHNA) was a gift from Dr. Elie Abushanab, University of Rhode Island, Kingstown, R.I. 5-iodotubercidin was from Research Biochemicals, Natick, Mass.; $N^6$-(benzyl)adenosine and $N^6$-(azidobenzyl) adenosine were generously provided by Dr. A. R. P. Paterson, University of Alberta, Edmonton, Alberta, Canada. All other chemicals and compounds were obtained from either the Sigma Chemical Co. or Fisher Scientific.

Source of T. gondii. Tachyzoites of the RH strain of T. gondii were propagated by intraperitoneal passage in female Swiss-Webster mice (Sasco, Inc., Omaha, Nebr.) as previously described [Iltzsch, M. H., Pyrimidine Salvage pathways in Toxoplasma gondii. J Euk. Microbiol., 40, pp. 24–28 (1993).]

Preparation of cytosol extracts. For the structure activity relationships studies, approximately $5 \times 10^8$ T. gondii were suspended in 1.2 ml of 50 mM N-2-hydroxyethylpiperazine-N'-2-ethanesulfonic acid (HEPES)-Cl (pH 8.0)/1 mM dithiothreitol and homogenized for 30 seconds at setting 10, using a Brinnmann Instruments Polytron homogenizer fitted with a PTA 7K1 probe. The homogenate was then centrifuged at approximately 116,000 g for 1 hour at 5° and the supernatant (cytosol extract) collected and used as the enzyme source. Fresh cytosol extracts were prepared for each experiment.

Adenosine kinase assay. T. gondii adenosine kinase activity was measured by following the formation of [$^{14}$C]AMP from [$^{14}$C]adenosine and ATP. Initial studies to set up the optimal assay conditions indicated that the apparent $K_m$ for adenosine is approximately 5 $\mu$M, the optimal concentration of $MgCl_2$/ATP is 0.5 mM each, and the optimal pH is 8.0. It should be noted that ATP containing vanadium (about 40 ppm) was used in all assays because the use of "vanadium-free" ATP resulted in low enzyme activity. The addition of 25 $\mu$M of (+)-EHNA or 100 $\mu$M of (±)EHNA was also found to be required to inhibit any contaminating adenosine deaminase activity which may degrade the substrate adenosine to inosine. Therefore, the standard reaction mixture contained 50 mM HEPES-Cl (pH 8.0), 1 mM dithiothreitol, 5 $\mu$M [8-$^{14}$C]adenosine (45 Ci/mol), 0.5 mM ATP, 0.5 mM $MgCl_2$, 25 $\mu$M (+)-EHNA or 100 $\mu$M (±)-EHNA, 10–30 $\mu$l of cytosol extract (approximately 3–10 $\mu$g of protein), and either 0, 0.1, 0.25, 0.5 or 1.0 mM of the compound to be tested, in a final volume of 150 $\mu$l. In order to more accurately determine appKi values, lower concentrations of the compound to be tested were used for very potent inhibitors or inhibitors that were poorly soluble, while higher concentrations were used for poor inhibitors. When compounds 9, 21, 22, 42, 47 and 48 (See Table 1) were tested, reaction mixtures (including those with no compound) contained 10% dimethyl sulfoxide (in addition to the standard reaction mixture) in order to ensure the solubility of these compounds.

Reactions were started by the addition of [8-$^{14}$C] adenosine, incubated at 37° for 10 minutes and terminated by placing the reaction tubes in a boiling water bath for 2 minutes. Precipitated proteins were removed by centrifugation in a microcentrifuge (approximately 13,000 g) for 5 minutes, and a 15 $\mu$l aliquot of the resulting supernatant was mixed with 5 $\mu$l of a solution containing 10 mM each of AMP and adenosine. This mixture was then spotted on silica gel thin layer chromatography plates which were developed with a mixture of chloroform/methanol/acetic acid (16:3:1). The average $R_f$ values for AMP and adenosine were 0.0 and 0.37, respectively. The substrate and product spots (which accounted for all of the radioactivity on the plates) were identified by UV quenching, cut out, and the radioactivity quantitated by liquid scintillation counting in 20 ml of Scintilene, using a Packard 460 scintillation counter. Under these conditions, velocity was linear with respect to time and amount of cytosol extract. Enzyme velocity was calculated by multiplying the fraction of AMP formed from adenosine times the amount of adenosine in the assay, and dividing by the incubation time.

Determination and significance of $AppK_i$ values. $AppK_i$ values were used to determine the relative degree of binding of compounds to adenosine kinase as compared to adenosine. $AppK_i$ values were estimated from Dixon plots of the data (1/v versus [I]), using a computer program with least squares fitting according to the general principles of Cleland (Cleland, W W, The statistical analysis of enzyme kinetic data. Adv. Enzymol. 29:1–32, 1967). The program was written by Dr. Sungman Cha (Brown University, Providence, R.I.) and modified to fit IBM BASIC by Dr. Fardos N. M. Naguib. If a compound is a competitive inhibitor with respect to adenosine, $appK_i$ values are related to $K_i$ values by the following equation: $appK_i = K_i(1+[S]/K_m)$. In the present study, the concentration of adenosine (5 $\mu$M) was approximately equal to the $K_m$ value. Thus, the $appK_i$ value determined for a competitive inhibitor would be about 2-fold higher than the $K_i$. It should be noted, however, that the type of inhibition (i.e., competitive, noncompetitive, or uncompetitive) produced by the compounds was not determined, nor were the compounds evaluated as substrates for T. gondii adenosine kinase.

Protein determinations. Protein concentrations were determined by the method of Bradford, M. M. [a rapid and sensitive method for the quantitation of microgram quantities of protein utilizing the principle of protein-dye binding. Anal. Biochem., 72: 248–254 (1976)], using the Bio-Rad Laboratories protein assay kit and bovine serum albumin as a standard.

EXAMPLE 2

Structure-Activity Relationship of the Binding of Nucleobase Ligands to Xanthine or Guanine Phosphoribosyltransferase from Toxoplasma gondii Chemicals and supplies. The source of the compounds screened as inhibitors of xanthine and guanine phosphoribosyltransferase are indicated in Table 3 by the following abbreviations: ALD, Aldrich Chemical Co., Inc., Milwaukee, Wis.; BWC, Burroughs Wellcome Co., Research Triangle Park, N.C.; CDC, Chemical Dynamics Corp., South Plainfield, N.J.; SHC, Dr. Shih-Hsi Chu, Brown University, Providence, R.I.; FLU, Fluka Chemical Co., Ronkonkoma, N.Y.; NBC, Nutritional Biochemicals Corp., Cleveland, Ohio; SIG, Sigma Chemical Co., St. Louis, Mo. [8-$^{14}$C] adenine (55 Ci/mol), [8-$^{14}$C] guanine (55 Ci/mol), [8-$^{14}$C] hypoxanthine (55 Ci/mol) and [8-$^{14}$C] xanthine (55 Ci/mol0 were obtained from Moravek Biochemicals, Inc., Brea Calif.; cellulose CEL 300 $UV_{254}$ Polygram thin layer chromatography plates were from Brinkmann, Westbury, N.Y.; and Bio-Rad protein assay kits were from Bio-Rad Laboratories, Richmond, Calif. All other chemicals and compounds were obtained from the Sigma Chemical Company.

Maintenance of T. gondii. Tachyzoites of the RH strain of T. gondii were propagated by intraperitoneal passage in female CD1 mice weighing 20–25 g (Charles River Laboratories, Wellington, Mass.). Mice were injected intraperitoneally (i.p.) with an inoculum ($10^6$ cells) of *T. gondii* ($10^6$ parasites) contained in 0.2 ml of sterile phosphate buffered saline (PBS), pH 7.2, and were sacrificed after 2–3 days by inhalation of ether. The parasites were harvested from the peritoneal cavity by injection, aspiration and reinjection of 3–5 mL of PBS (2–3 times). The peritoneal fluid was examined microscopically to determine the concentration of *T. gondii* and to ascertain the extent of contamination by host cells. Two-day transfers generally produced parasite preparations that contained very little contamination and had a viability of >97%.

Preparation of enzyme extracts. *T. gondii* suspension in phosphate-buffered saline was washed 2–3 times in 50 mM Tris-Cl, pH 7.4, at room temperature. Enzyme extracts were prepared by sonicating live parasites in 3 volumes of 50 mM Tris-Cl, pH 7.4, using a Fisher Sonic Dismembrator (Model 300) on ice. The sonicate (enzyme extract) was used as the enzyme source.

Phosphoribosyltransferase assays. Phosphoribosyltransferase activity from *T. gondii* was measured by following the formation of [$^{14}$C] nucleoside 5'-monophosphate (and [$^{14}$C] nucleoside formed by phosphohydrolase acitivity from [$^{14}$C] nucleobase and 5-phosphoribosyl-1-pyrophosphate (PRibPP). The standard reaction mixtures contained 50 mM Tris-Cl (pH 7.4), 10 $\mu$M [8-$^{14}$C]xanthine (55 Ci/mol) or 4 $\mu$M [8-$^{14}$C]guanine (55 Ci/mol), 4 mM PRibPP, 20 mM $MgCl_2$, 50 mM KCI, and 50 $\mu$l of enzyme extract (4–8 $\mu$g of protein) in a final volume of 100 $\mu$l. When analogues were being tested, various concentrations (0–0.9 mM) of the analogue were also included.

Reactions were incubated at 37° C. and terminated in boiling water bath for 2 minutes. Precipitated proteins were removed by centrifugation. A 10 $\mu$l aliquot of the resulting supernatant was spotted on cellulose thin layer chromatography plates which were developed with 5% dibasic potassium phosphate. The average $R_f$ values were as follows: hypoxanthine, 0.49; inosine, 0.65; IMP, 0.77; guanine, 0.14; guanosine, 0.57; GMP, 0.70; xanthine, 0.46; xanthosine, 0.61; XMP, 0.74; adenine, 0.33; adenosine, 0.46; AMP, 0.67. The radioactivity was quantified using a Berthold TLC Linear Analyzer (Wallac Inc., Gaithersburg, Md.). All assays were run under conditions in which velocity was linear with respect to time and amount of enzyme extract. Exzyme velocity was calculated by multiplying the fraction of nucleotide plus nucleoside formed from nucleobase by the amount of nucleobase in the assay divided by the incubation time. Specific activity was estimated by dividing enzyme velocity by the amount of protein in the assay.

Determination of apparent $K_m$ values. The assay conditions were the same as for the standard assay except for the substrate concentrations used. The range of substrate concentrations was 1–7 $\mu$M. Apparent $V_{max}$ and $K_m$ values were calculated using a computer program written by Dr. Sungman Cha (Brown University, Providence, R.I.) and fitted into IBM BASIC by Dr. Fardos N. M. Naguib. This program employs the Wilkinson-Cleland procedure [Wilkinson, G. N., Statistical Estimations in Enzyme Kinetics, *Biochem. J.*, 80:324–332, 1961; and Cleland, W. W., The Statistical Analysis of Enzyme Kinetic Data, *Adv. Enzymol.*, 29:1–32, 1967] for the estimation of $V_{max}$ and $K_m$.

Determination and significance of apparent $K_i$ values. Apparent $K_i$ values were estimated from Dixon plots of the data (1/v versus (I)) using a computer program that employs least-squares fitting according to the general principles of Cleland (Cleland, W W The statistical analysis of enzyme kinetic data. *Adv Enzymol* 29: 1–32, 1967). This program was developed by Drs. S. Cha and F. N. M. Naguib. If a compound is a competitive inhibitor with respect to the substrate, apparent $K_i$ values are related to $K_i$ values by the following equation: Apparent $K_i = K_i(1+(S)/K_m)$. In the present study, the concentration of the purine nucleobase (10 $\mu$M and 4 $\mu$M for xanthine and guanine, respectively) was about 3-fold greater than its approximate apparent $K_m$ value (Table 1) and the concentration of PRibPP (4 mM) was at a saturating concentration (results not shown). Thus, the apparent $K_i$ value determined for a competitive inhibitor would be about 4-fold higher than the $K_i$. It should be noted, however, that the type of inhibition (i.e. competitive, noncompetitive, or uncompetitive) produced by the compounds was not determined.

Protein determinations. Protein concentrations were determined by the method of Bradford, M. M. [a rapid and sensitive method for the quantitation of microgram quantities of protein utilizing the principle of protein-dye binding. *Anal. Biochem.*, 72: 248–254 (1976)], using the Bio-Rad Laboratories protein assay kit and bovine serum albumin as a standard.

EXAMPLE 3

Metabolism and Toxicity of 6-Substituted 9-β-D-Ribofuranosylpurines in *Toxoplasma Gondii*

Chemicals and supplies. [G-$^{13}$H]NBMPR (36 Ci/mmol), [5,6-$^{13}$H]uracil (38 Ci/mmol) and [8-$^{14}$C]adenosine (45 Ci/mol) were purchased from Moravek Biochemicals, Brea, Calif., 5- iodotubercidin was from Research Biochemicals, Natick, Mass.; N6-(benzyl)adenosine and N6-(azidobenzyl) adenosine were generously provided by Dr. A. R. P. Paterson, University of Alberta, Edmonton, Alberta, Canada; NBMPR-P was synthesized from NBMPR as described in Example 1; all other chemicals were purchased from Sigma, St. Louis, Mich.

Maintenance of *T. gondii*. The wild type RH, the adenosine kinase deficient mutant ara-$A^R$ (R), and the phosphoribosyltransferase deficient mutants (HGPRT$^-$ and Tnx$^{R-1}$) strains of *T. gondii* were propagated by intraperitoneal passage in female CD1 mice (20–25 g). Mice were injected intraperitoneally (i.p.) with an inoculum ($10^6$ cells) of *T. gondii* contained in 0.2 ml of sterile phosphate buffered saline (PBS), pH 7.2, and were sacrificed after 2–3 days by inhalation of ether. The parasites were harvested from the peritoneal cavity by injection, aspiration and reinjection of 3–5 mL of PBS (2–3 times). The peritoneal fluid was examined microscopically to determine the concentration of *T. gondii* and to ascertain the extent of contamination by host cells. Two-day transfers generally produced parasite preparations that contained very little contamination and had a viability of >95%.

While *T. gondii* were used for in vitro incorporation studies, the procedure was performed aseptically and the parasites were washed and resuspended in Dulbecco's modified Eagle medium (Gibco BRL) containing 100 units/mL penicillin G, 100 $\mu$g/mL streptomycin sulfate, and 3% FBS (fetal bovine serum) (HyClone Laboratories, Logan, Utah). For the purpose of enzyme studies, to ascertain the purity of *T. gondii* for enzyme isolation and purification, the parasites were purified from host cells and debris by coagulating the host cells by addition of 50 $\mu$L phytohemagglutinin P (Difco) to the suspension of the parasites in 5 mL of medium, shaking slowly for 15 minutes, filtering slowly through a 5 $\mu$m Nucleopore polycarbonate filter (Costar, Cambridge, Mass.) using trypan blue exclusion method and counting on a hemacytometer. These procedures produce parasite preparations that are >99% pure. The parasites were then pelleted by centrifugation, washed twice with PBS and resuspended in 1 mL of the appropriate homogenization buffer required by the enzyme to be assayed. Parasites that were not immediately used were stored frozen in PBS at −70° C.

Preparation of extracts. Extracts of *T. gondii* were prepared by homogenizing parasites or tissues in ice cold (3:1, v/w) 50 mM Tris-Cl buffer (pH 7.4) containing 1 mM EDTA, 1 mM dithiothreitol with a polytron homogenizer (Brinkmann, Westbury, N.Y.) and the homogenates were centrifuged at 105,000×g for 1 hour at 4° C. The supernatant fluids (cytosol) were collected and used as the enzyme source.

Conversion assays. To measure the percent conversion of NBMPR to NBMPR-P and nucleobase (NBMP) by extracts of *Toxoplasma gondii* and mouse spleen, 50 mM Tris-Cl (pH 7.4), 5 mM $MgCl_2$, 2.5 mM ATP, 5 mM creatine phosphate, creatine phosphokinase, 50 $\mu$M [$^3$H-(G)] NBMPR (1.95 $\mu$Ci/nmol), and 10 $\mu$l of cytosol extract were reacted in a final volume of 20 $\mu$l and incubated at 37° C. Reaction was initiated by addition of extract and terminated by boiling for 3 minutes. Results are reported in Table 5. In a second reaction, 25 mM KCN was added to the reaction mixture. Results are reported in Table 6.

Enzyme assay. Assays were run under conditions where activity was linear with time and enzyme concentrations. Activities were determined by following the formation of radiolabeled nucleotides and nucleobases from their respective nucleosides (adenosine or NBMPR). The assay mixture contained 50 mM Tris-Cl (pH 7.4), 5 mM $MgCl_2$, 2.5 mM ATP, 5 mM creatine phosphate, 50 $\mu$M [G-$^3$H] NBMPR (1.95 Ci/mmol) or 5 $\mu$M [8-$^{14}$C]adenosine (45 Ci/mol), and 50 $\mu$L of enzyme preparation in a final volume of 100 $\mu$L. When adenosine was used as a substrate, 25 $\mu$M of EHNA ((±)erythro-9-(2-S-3-R-nonyl)adenine), an inhibitor of adenosine deaminase, was included in the reaction mixture to inhibit any adenosine deaminase activity present. Incubation was carried out at 37° C. The reaction was terminated by boiling for 3 minute followed by freezing for at least 20 minutes. Proteins were removed by centrifugation and 10 $\mu$L of the supernatant fluid were spotted on Silica Gel TLC plates (Brinkmann, Westbury, N.Y.). The plates for adenosine kinase assay were then developed in a mixture of chloroform/methanol/acetic acid (102:12:6, v/v/v). The $R_f$ values were: adenosine, 0.27; adenine, 0.36; AMP, 0.17. The plates for the assays of NBMPR were developed in n-butanol/ethyl acetate/$NH_4$/methanol (49:28:28:21, v/v/v/v). The $R_f$ values were: NBMPR, 0.76; NBMPR-P, 0.50; NBMP, 0.89. The amounts of radioactivity in the substrate (nucleoside) and product (nucleobase and nucleotides) were calculated on a percentage basis using a Berthold LB-284 Automatic TLC-Linear Analyzer.

Phosphoribosyltransferase activity was measured by following the formation of [$^3$H] NMMPR-P from [$^3$H] NBMPR and 5-phosphoribosyl-1-pyrophosphate (PRPP). The standard reaction mixtures contained 50 mM Tris-Cl (pH 7.4), 10 $\mu$M [$^3$H] NBMPR (55 Ci/mol), 4 mM PRibPP, 20 mM $MgCl_2$, 50 mM KCI, and 50 $\mu$l of enzyme extract (4–8 $\mu$g of protein) in a final volume of 100 $\mu$l. Reactions were incubated at 37° C. and terminated in boiling water bath for 2 minutes. Precipitated proteins were removed by centrifugation. A 10 $\mu$l aliquot of the resulting supernatant was spotted on cellulose thin layer chromatography plates which were developed with 5% dibasic potassium phosphate. The average $R_f$ values were as follows: NBMPR, 0.28; NBMP, 0.16; NBMPR-P, 0.44. The radioactivity was quantified using a Berthold TLC Linear Analyzer (Wallac, Inc., Gaithersburg, Md.). All assays were run under conditions in which velocity was linear with respect to time and amount of enzyme extract. Enzyme velocity was calculated by multiplying the fraction of nucleotide formed from nucleoside by the amount of nucleoside in the assay divided by the incubation time. Specific activity was estimated by dividing enzyme velocity by the amount of protein in the assay.

Preparation of Samples for HPLC Analysis. The metabolism of NBMPR was also monitored in the acid-soluble fraction of the enzyme assays preparations. At the end of each incubation period, proteins were removed by centrifugation. The supernatant was collected and stored frozen at −20° C. until analyzed by HPLC.

HPLC Analysis. The analysis was performed on two Hypersil $C_{18}$ reverse phase (25×0.4 cm, ODS 5 $\mu$m) columns (Jones Chromatography, Littleton, Colo.) in tandem on a Hewlett-Packard 1050 liquid chromatograph system equipped with diode-array multiple wave length uv monitor. The system was operated by a computer program which handles data analysis, comparison and storage after each run. Elution was performed stepwise, using 2 mobile phases: 50 mM ammonium acetate in 0.5% acetonitrile, pH 4.8, (Buffer A), and 50 mM ammonium sulfate in 60% acetonitrile, pH 4.8, (Buffer B). A 25 $\mu$L sample was injected with Buffer A for 10 minutes, followed by a 120 minute linear gradient to 60% Buffer B, then a 10 minute isocratic elution by 40% Buffer A-60% Buffer B. Flow rate was 1 ml/min, except, from 5–10 minutes and 120–132 minutes it was 0.5 mL/min. The eluent was monitored at 254 nm and $\lambda_{max}$ of the compound under study. Under these conditions, NBMPR-P eluted at 86–87 minutes, NBMPR eluted at 102–103 minutes; the nucleobase, NBMP (pk 6), eluted at 106–107 minutes; and a fourth, unknown, peak eluted (pk 7) at 111–112 minutes.

Mass Spectrometry Analysis. Analysis of NBMPR metabolites was performed on an API III triple quadrupole Perkin-Elmer SCIEX LC/MS/MS mass spectrometer. The metabolites of NBMPR, pk 6 and pk 7, were separated by reverse phase HPLC on 100×2.1 mm Aquapore $C_8$ column at a flow rate of 0.2 mL/min, using a 0–50% acetonitrile gradient (5% per minute) in aqueous ammonium acetate. The elute was split 1:1 with 100 $\mu$L/min going to the electrospray interface. Positive and negative ion mass spectra were recorded in this mode. The LCMS analysis of the pk 6 (presumed to be the nucleobase, NBMP) produced two molecular species of weights 287 and 403. The LCMS analysis of unknown pk 7 produced a molecular weight of 358.

Incorporation of Radiolabeled Uracil. Uracil uptake assays are highly specific to *T. gondii* as mammalian cells do not incorporate uracil into either their nucleoside and nucleotide pool, or nucleic acids. An exponential increase in radiolabel incorporation closely correlated with the exponential growth of the parasite. Uptake and incorporation of radiolabeled uracil into nucleic acids of *T. gondii* were carried out, at least in triplicates, in tissue culture, using monolayers of human foreskin fibroblasts infected with *T. gondii*. The fibroblasts were cultured in no more than 30 passages in Dulbecco's modified Eagle medium, containing 100 units/mL penicillin G and 100 $\mu$g/mL streptomycin sulfate, and 10% FBS, pH 7.2. Briefly, confluent cells (4–5 day incubation) were cultured for 24 hours in the 24-well flat bottom microtiterplates (~5×10$^5$/1 mL/well) and incubated at 37° C. in 5% $CO_2$, 95% air to allow the cells to attach. The medium was then removed and the cells were infected with isolated *T. gondii* in medium with 3% FBS (1 parasite/cell).

After 1 hour incubation, the cultures were washed with media with 10% FBS to remove extracellular parasites. FBS was maintained at a final concentration of 10%. Five concentrations of the compound were then added to cultures of the parasite-infected cells to give a final concentration of 0, 5, 10, 25 and 50 μM. Drugs were dissolved in 50% ethanol to give a final concentration of 2.5% ethanol when added to the wells. After an additional 18 hours incubation, the medium was replaced with 1 mL drug free media containing [5,6-$^{13}$H]uracil (2 μCi/mL) and incubated for another 6 hours, after which the media was removed. The fibroblasts were released from the wells by trypsinization with the addition of 200 μL trypsin/EDTA (2.5×) to each well. After 10 minutes incubation, 1 mL of ice cold 10% trichloroacetic acid (TCA) was added to each well. The plates were then placed on a shaker to insure the detachment of the cells. The suspended contents of each well were filtered through GF/A 2.4 cm glass microfiber filters (Whatman, Hillsboro, Oreg.), which were prewashed each with 1 mL double distilled $H_2O$ and dried. After filtration, the filters were washed with 10 mL methanol, left to dry, and then placed in scintillation vials containing 5 mL of Econo-Safe scintillation fluor (Research Products International Corp., Mount Prospect, Ill.), and radioactivity was counted using an LS5801 Beckman scintillation counter.

Toxicity of compounds. Toxicity of the different doses of the various analogues were performed at least in triplicates, using a modification of the Microculture Tetrazolium (MTT) assay and uninfected monolayers of human foreskin fibroblasts. Briefly, confluent cells were incubated for at least 24 hours in the 96-well flat bottom microtiterplates (~$10^5$/200 μL/well) and incubated at 37° C. in 5% $CO_2$, 95% air to allow the cells to attach. The medium was then replaced with 200 μL of fresh medium. The appropriate concentration of the compounds was dissolved in 50 μL of medium and added to each well to give final concentrations of 0, 5, 10, 25, and 50 μM. The cultures were then incubated for 48 hours, after which 50 μL of sterile MTT solution (2 mg/1 mL PBS) was added to each well. MTT solution was sterilized by filtration through 0.22 μm filters (Costar, Cambridge, Mass.). After 4 hours incubation, the medium was removed and 100 μL of dimethylsulfoxide (DMSO) was added to each well and the plates were shaken gently for 2–3 minutes to dissolve the formed formazan crystals. The absorbance was measured at 540 nm, using a computerized microtiterplate reader (Themomax, Molecular Division)

Chemotherapy of Toxoplasma-Infected Mice. Female CD-1 mice, approximately 22 g (Charles River Laboratories, Wilmington, Mass.), were infected with 200 RH strain tachyzoites/mouse by i.p. injection. The treatment group received 100 mg/kg NBMPR-P i.p. injections every 8 hours on Days 0, 2, 4 and 5, in proportion of 0.1 ml/10 g. Mice were maintained under controlled temperature (25° C.) and light (12/12 hours, light/dark), food and water ad libitum, and survival was monitored daily.

Results

Table 5 shows that extracts of *T. gondii*, unlike extracts of mouse spleen, is capable of converting nitrobenzylthioinosine or 6-[(4-nitrobenzyl)thio]-9-β-D-ribofuranosylpurines (NBMPR) to its nucleoside 5'-monophosphate, NBMPR-P, and its nucleobase, nitrobenzylmercaptopurine (NBMP). The formation of these metabolites increased with the incubation time. The authenticity of the nucleotide and nucleobase formation was verified by HPLC and MS/MS/LC analyses.

TABLE 5

Percent conversion of NBMPR to NBMPR-P and nucleobase (NBMP) by extracts of *Toxoplasma gondii* and mouse spleen

| Product | Period of Incubation (min) | | | | |
|---|---|---|---|---|---|
| | 15 | 30 | 60 | 120 | 240 |
| NBMPR-P | | | | | |
| *T. gondii* | 2.1 ± 0.5 | 3.2 ± 0.4 | 7.8 ± 1.5 | 9.4 ± 1.0 | 15.1 ± 4.4 |
| Mouse | 0 | 0 | 0 | 0 | 0 |
| NBMP | | | | | |
| *T. gondii* | 8.0 ± 0.4 | 7.8 ± 3.7 | 14.8 ± 1.2 | 9.4 ± 2.8 | 10.4 ± 6.2 |
| Mouse | 0 | 0 | 0 | 0 | 0 |

Since it is known that NBMPR could be oxidized to 6-mercaptopurine riboside which is cleaved to 6-mercaptopurine, which is then converted to 6-mercaptopurine 5'-monophosphate by hypoxanthine-guanine phosphoribosyltransferase [EC2.4.2.8], the conversion of NBMPR to NBMPR-P and NBMP was tested in the presence of KCN, an inhibitor of oxidation. The results in Table 6 indicate that KCN had no significant effect on the formation of these metabolites.

TABLE 6

Percent conversion of NBMPR to NBMPR-P and NBMP by extracts of *Toxoplasma gondii* in the presence of 25 mM KCN.

| Product | Period of Incubation (min) | | | | |
|---|---|---|---|---|---|
| | 15 | 30 | 60 | 120 | 240 |
| NBMPR-P | 0.5 ± 0.1 | 1.1 ± 0.1 | 3.7 ± 2.5 | 5.8 ± 0.7 | 11.8 ± 4.8 |
| NBMP | 0.9 ± 0.3 | 2.8 ± 3.8 | 4.0 ± 1.3 | 9.5 ± 1.3 | 14.3 ± 3.3 |

To investigate by which enzyme NBMPR is converted to NBMPR-P, the effect of various natural substrates and inhibitors of several enzymes of the purine salvage pathways which could be involved in the metabolism of NBMPR were tested. Tables 7 and 8 show that adenosine inhibits the formation of NBMPR-P from NBMPR by extracts of *T. gondii*, while inosine has a minimal effect. Adenine or hypoxanthine at 1 mM had no effect on the phosphorylation of NBMPR. These results suggest that adenosine kinase is the enzyme responsible for the direct phosphorylation of NBMPR.

TABLE 7

Percent inhibition by different concentrations of adenosine on the formation of NBMPR-P from NBMPR by extracts of *Toxoplasma gondii*

| NBMPR | Adenosine [μ] | | |
|---|---|---|---|
| [μM] | 50 | 75 | 150 |
| 25 | 66 | 96 | 100 |
| 50 | 85 | 91 | 98 |

TABLE 8

Percent inhibition by different concentrations of NBMPR on the formation of nucleosides 5'-monophosphate from adenosine and inosine by extracts of *Toxoplasma gondii*.

| | NBMPR [μM] | | |
|---|---|---|---|
| Compound | 10 | 100 | 1000 |
| Adenosine | 77 | 100 | 100 |
| Inosine | 15 | 19 | ND[a] |

[a]ND, not determined.

Therefore, the effect of NBMPR, iodotubercidin (an inhibitor of adenosine kinase), formycin A (an inhibitor of 5'-methylthioadenosine phosphorylase, EC 2.4.2.28), and 8-aminoguanosine (an inhibitor of purine nucleoside phosphorylase) on the phosphorylation of adenosine were investigated. Table 6 shows that formycin A and 8-aminoguanosine had no effect on the phosphorylation of adenosine by extracts from *T. gondii*, human liver, or mouse liver. Only NBMPR affected the phosphorylation of adenosine in *T. gondii*, but not in human or mouse livers. Iodotubercidin, on the other hand, inhibited the phosphorylation of adenosine by extracts from all three tissues.

TABLE 9

Percent inhibition by different concentrations of various concentrations of NBMPR and Iodotubercidin on the phosphorylation of adenosine by extracts from *Toxoplasma gondii*, human and mouse liver.

| | % Inhibition | | |
|---|---|---|---|
| Compound | *T. gondii* | Human Liver | Mouse Liver |
| NBMPR | | | |
| 10 μM | 3.4 | 0 | 0 |
| 25 μM | 37.7 | 0 | 0 |
| 50 μM | 56.0 | 0 | 0 |
| Iodotubercidin | | | |
| 10 μM | 82.9 | 95.9 | 97.2 |
| 25 μM | 85.6 | 100 | 97.5 |

Similarly, the data on Table 10 shows that only iodotubercidin inhibited the phosphorylation of NBMPR in *T. gondii*.

TABLE 10

Percent inhibiton by different concentrations of various inhibitors on the phosphorylation of NBMPR by extracts of *Toxoplasma gondii* and human liver.

| | % Inhibition | |
|---|---|---|
| Compound | *T. gondii* | Human Liver |
| Iodotubercidin | | |
| 10 μM | 74.8 | 87.2 |
| 25 μM | 60.0 | 75.6 |
| 50 μM | 66.5 | 78.1 |
| Formycin A | | |
| 100 μM | 0 | 0 |
| 250 μM | 0 | 0 |
| 500 μM | 0 | 0 |
| 8-Aminoguanosine | | |
| 25 μM | 0 | 0 |
| 50 μM | 0 | 0 |
| 100 μM | 0 | 0 |

Table 11 shows that only the RH wild type strain can phosphorylate adenosine and NBMPR to their respective nucleoside 5'-monophosphate. Extracts from the adenosine kinase deficient mutant, ara-A$^R$, had little activity with either substrate. These results indicate that adenosine kinase in toxoplasma is the enzyme responsible for the direct phosphorylation of NBMPR.

TABLE 11

Phosphorylation of Adenosine and NBMPR by extracts from RH wild type strain and adenosine kinase deficient ara-A$^R$ mutant strain of *T. gondii*.

| | Substrate | |
|---|---|---|
| Strain | Adenosine | NBMPR |
| RH | 309.8 ± 3.2[a] | 248.9 ± 15.7 |
| ara-A$^R$ | 4.3 ± 1.2 | 2.5 ± 0.1 |

[a]fmol/min/mg protein.

To demonstrate that NBMPR can be metabolized by adenosine kinase and/or a phosphoribosyltransferase, the formation of NBMPR-P from NBMPR was assayed in the presence of ATP (kinase route) or PRPP (phosphoribosyltransferase route) in two types of mutants. These mutants either lack adenosine kinase (Ara-A$^R$) or hypoxanthine-guanine phosphoribosyltransferase (HGPRT$^-$ or Thx$^{R-1}$). The results (Table 12) indicate that in the presence of ATP and absence of the phosphoribosyltransferase, i.e. HGPRT$^-$ or Thx$^{R-1}$, NBMPR-P was formed. Similarly, in the presence of PRPP and absence of adenosine kinase, i.e. Ara$^R$, NBMPR-P can still be formed indicating that the phosphoribosyltransferase route is active. This is a strong indication that NBMPR-P can be formed by both the kinase and phosphoribosyltransferase reactions in *T. gondii*.

TABLE 12

Percent conversion of NBMPR to NBMPR-P in the presence of ATP or PRPP by extracts from different strains of Toxoplasma

| Strain | +ATP | +PRPP |
|---|---|---|
| RH | 0.7 ± 0.2 | 4.3 ± 0.3 |
| Ara-A$^R$ | 0 | 3.8 ± 0.2 |
| HGPRT$^-$ | 2.6 ± 1.3 | 0 |
| Thx$^{R-1}$ | 2.0 ± 0.6 | 0 |

To investigate the effect of metabolizing NBMPR on the survival of *T. gondii*, the number and size of plaque formation by *T. gondii* on human fibroblasts was investigated. NBMPR decreased the number and size of toxoplasma in human fibroblasts (Table 13).

TABLE 13

Effect of different concentrations of NBMPR on number of plaques formed by *Toxoplasma gondii* grown in human fibroblasts in culture.

| NBMPR [μM] | Number of Plaques |
|---|---|
| 0 | 21 ± 3.5 |
| 33 | 23 ± 0.7 |
| 100 | 3 ± 1.4 |

The growth of toxoplasma was also inhibited by NBMPR and NBMPR-P and the inhibition was dose dependent (Table 14). These two compounds had no significant toxic effect on the survival of host cells (Table 15). These results indicate that NBMPR or NBMPR-P could be used as therapeutic agents against toxoplasma. Indeed, administration of NBMPR-P to mice infected with toxoplasma was found to increase their life span from 6 to 8 days (Table 13).

TABLE 14

Effect of treatment with NBMPR-P on the survival of mice infected with *Toxoplasma gondii*.

| Treatment | Day 6 | Day 7 | Day 8 | Day 9 |
|---|---|---|---|---|
| None | 0/3 | | | |
| NBMPR-P | 3/3 | 3/3 | 2/3 | 0/3 |

Each mouse was infected with 200 tachyzoites and the treatment group received 100 mg/kg NBMPR-P i.p. injections every 8 hours on Days 0, 2, 4 and 5 in proportion of 0.1 ml/10 g. The survivorship of the treated mice can be improved by manipulation of the dose and regimen of NBMPR.

Because of the potentiality of NBMPR in the treatment of toxoplasma, several 6-substituted 9-β-D-ribofuranosylpurines were tested as anti-toxoplasmic agents in vitro. Among the analogues tested, nitrobenzyl-6-selenopurine riboside, $N^6$-benzyladenosine, $N^6$-(azidobenzyl)adenosine and $N^6$-(nitrobenzyl)adenosine were promising (Table 14). These four compounds were comparable or better agents than sulfadiazine, or pyrimethamine, the standard chemotherapeutic agents for the treatment of toxoplasmosis.

TABLE 15

Effect of various 6-substituted 9-β-D-ribofuranosylpurines and other therapeutic compounds on percent survival of *Toxoplasma gondii* grown in human fibroblasts in culture.

| Compound | Concentration [μM] | | | | |
|---|---|---|---|---|---|
| | 0 | 5 | 10 | 25 | 50 |
| NBMPR | 100 | 74.3 | 55.5 | 23.1 | 6.7 |
| NBMPR-P | 100 | 75.3 | 53.3 | 21.4 | 10.2 |
| Nitrobenzyl-6-selenopurine riboside | 100 | 67.8 | 3.03 | 0 | 0 |
| $N^6$-Anisoyladenosine | 100 | 94.2 | 93.1 | 104.2 | 125.4 |
| $N^6$-Benzoyladenosine | 100 | 96.4 | 94.6 | 111.7 | 100.5 |
| $N^6$-Benzyladenosine | 100 | 62.8 | 41.8 | 52.9 | 26.3 |
| $N^6$-(Aminobenzyl) adenosine | 100 | 100.0 | 95.6 | 108.3 | 119.9 |
| $N^6$-(Azidobenzyl) adenosine | 100 | 36.9 | 17.0 | 15.1 | 24.5 |
| $N^6$-(Nitrobenzyl) adenosine | 100 | 35.9 | 27.6 | 21.6 | 8.4 |
| Sulfadiazine | 100 | 74.6 | 64.8 | 66.3 | 66.3 |
| Pyrimethamine | 100 | 25.9 | 12.9 | 10.2 | 13.8 |

TABLE 15-continued

Effect of various 6-substituted 9-β-D-ribofuranosylpurines and other therapeutic compounds on percent survival of *Toxoplasma gondii* grown in human fibroblasts in culture.

| Compound | Concentration [μM] | | | | |
|---|---|---|---|---|---|
| | 0 | 5 | 10 | 25 | 50 |

Survival was measured by incorporation of [5,6-$^3$H] uracil from at least 2 experiments of 4 replica each.

However, $N^6$-benzyladenosine, unlike the other three compounds, was toxic to host cells at therapeutic doses (Table 16).

TABLE 16

Effect of various 6-substituted 9-β-D-ribofuranosylpurines and other therapeutic compounds on percent survival of uninfected human fibroblasts grown in culture.

| Compound | Concentration [μM] | | | | |
|---|---|---|---|---|---|
| | 0 | 5 | 10 | 25 | 50 |
| NBMPR | 100 | 98.8 | 97.1 | 96.3 | 95.4 |
| NBMPR-P | 100 | 103.3 | 94.6 | 93.6 | 96.1 |
| Nitrobenzyl-6-selenopurine riboside | 100 | 89.3 | 90.1 | 63.4 | 39.6 |
| $N^6$-Anisoyladenosine | 100 | 92.9 | 92.6 | 99.2 | 97.4 |
| $N^6$-Benzyladenosine | 100 | 46.3 | 21.8 | 36.5 | 31.0 |
| $N^6$-Benzoyladenosine | 100 | 94.4 | 94.1 | 97.6 | 99.3 |
| $N^6$-(Aminobenzyl) adenosine | 100 | 93.3 | 91.9 | 100.6 | 101.4 |
| $N^6$-(Azidobenzyl) adenosine | 100 | 97.3 | 90.3 | 88.9 | 81.5 |
| $N^6$-(Nitrobenzyl) adenosine | 100 | 104.1 | 102.1 | 92.3 | 106.8 |
| Sulfadiazine | 100 | 98.2 | 99.7 | 99.8 | 102.5 |
| Pyrimethamine | 100 | 103.6 | 98.8 | 108.2 | 118.4 |

Survival was measured by absorbance at 540 nm of MTT treated cells from at least two experiments each of 4 replica.

Equivalents

Those skilled in the art will recognize or be able to ascertain using no more than routine experimentation, many equivalents of the specific embodiments of the invention described herein. Such equivalents are intended to be encompassed by the following claims.

We claim:

1. A method of treating a host infected with *Toxoplasma gondii*, comprising the step of administering to said host a therapeutically effective amount of a composition comprising a compound which is an α or β anomer, a D(+) or L(−) enantiomer of the following structural formula:

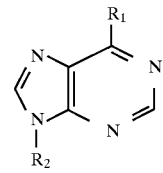

wherein, $R_1$ is a halogen, $OR_6$, $SR_6$, $SeR_6$ or $CH_2R_6$ and $R_6$ is alkyl, alkene, arylalkyl or aryl and wherein $R_6$ is not nitrobenzyl;

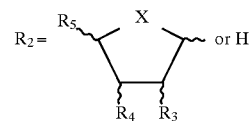

X is $CH_2$, O or S;

$R_3$ is H, OH or a halogen;

$R_4$ is H, OH or a halogen; and $R_5$ is $CH_3$, $CF_3$, $CH_2OH$ or $CH_2OY$ and Y is a carbon ester or phosphorus and a pharmaceutically acceptable carrier.

2. The method of claim 1 wherein, said composition contains a compound selected from the group consisting of 6-chloropurine riboside 3'-deoxysangivamycin $N^6$-(p-methoxybenzoyl) adenosine, $N^6$-benzyladenosine, $N^6$-azidobenzyladenosine and 7-deazahypoxanthine, 7-deazaxanthine, 7-deaza-6-thiopurine, 7-deaza-2-amino-6-thiopurine and 7-deaza-2-oxo-6-thiopurines.

3. A method of treating an animal infected with a parasite, wherein said parasite primarily utilizes a purine salvage pathway to generate purines, comprising the step of: administering to said animal a therapeutically effective dose of a composition comprising a compound which is an α or β-anomer, a D(+) or L(-) enantiomer of the following structural formula:

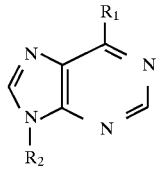

wherein, $R_1$ is a halogen, $OR_6$, $SR_6$, $SeR_6$ or $CH_2R_6$ and $R_6$ is alkyl, alkene, arylalkyl or aryl and wherein $R_6$ is not nitrobenzyl;

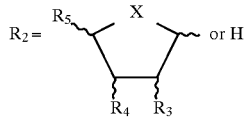

X is $CH_2$, O or S;

$R_3$ is H, OH or a halogen;

$R_4$ is H, OH or a halogen; and $R_5$ is $CH_3$, $CF_3$, $CH_2OH$ or $CH_2OY$ and Y is a carbon ester or phosphorus and a pharmaceutically acceptable carrier.

4. A method of treating a host having toxoplasmosis, comprising the step of administering to said host a therapeutically effect dose of a composition comprising a compound which is an α or β anomer, a D(+) or L(-) enantiomer of the following structural formula:

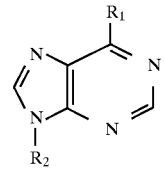

the composition of claim 1.

5. A pharmaceutical composition comprising a compound which is an α or β anomer, a D(+) or L(-) enantiomer of the following structural formula:

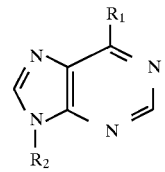

wherein, $R_1$ is a halogen, $OR_6$, $SR_6$, $SeR_6$ or $CH_2R_6$ and $R_6$ is alkyl, alkene, arylalkyl or aryl and wherein $R_6$ is not nitrobenzyl;

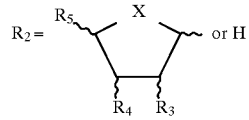

X is $CH_2$, O or S;

$R_3$ is H, OH or a halogen;

$R_4$ is H, OH or a halogen; and $R_5$ is $CH_3$, $CF_3$, $CH_2OH$ or $CH_2OY$ and Y is a carbon ester or phosphorus and a pharmaceutically acceptable carrier.

6. The composition of claim 5 wherein said composition contains a compound selected from the group consisting of 6-chlorosporine riboside 3'-deoxysangivamycin $N^6$-(p-methoxybenzoyl)adenosine, and $N^6$-benzyladenosine.

7. The method of one of claims 1 or 3, wherein said host is a human.

* * * * *

UNITED STATES PATENT AND TRADEMARK OFFICE
CERTIFICATE OF CORRECTION

PATENT NO. : 5,773,424  Page 1 of 2

DATED : June 30, 1998

INVENTOR(S) : M. H. El Kouni, et al.

It is certified that error appears in the above-identified patent and that said Letters Patent is hereby corrected as shown below:

On The Title Page, [56] References Cited: Insert
--OTHER PUBLICATIONS

Drugs 38 (6), Robert E. McCabe and Sharon Oster, Current Recommendations and Future Prospects in the Treatment of Toxoplasmosis, 1989, pp. 973-987.

J. Parasitol, 64 (3), E.R. Pfefferkorn and Lorraine C. Pfefferkorn, The Boichemical Basis for Resistance to Adenine Arabinoside in a Mutant of Toxoplasma Gondll, 1978, pp. 486-492.

Acta Tropica 39, P.O.J. Ogbunude and C.O. Ikediobi, Effect of Nitrobenzylthioinosinate on the Toxicity of Tubercidin and Ethidium Against Trypanosoma Gambiense, 1982, pp. 219-224.

Biochemical Pharmacology, Vol. 36, No. 22, Mahmoud H. el Kouni, Norna J. Messier and Sungman Cha, Treatment of Schistosomiasis by Purine Nucleoside Analogues in Combination with Nucleoside Transport Inhibitors, 1987, pp. 3815-3821.

Drugs Exptl. Clin. Res. XVIII (10), P.O.J. Ogbunude and M.H. Al-Jasser, Experimental Chemotherapy of Leishmaniasis with Adenosine Analogue Formycin A, in Combination with Inhibitor of Nucleoside Transport, Nitrobenzylthioinosinate, 1992, pp. 423-426.

The Journal of Infectious Disease, Vol. 154, No. 4, Benjamin J. Luft, Potent in Vivo Activity of Aprinocid, a Purine Analogue, Against Murine Toxoplasmosis, 1986, pp. 692-694.

UNITED STATES PATENT AND TRADEMARK OFFICE
CERTIFICATE OF CORRECTION

PATENT NO. : 5,773,424
DATED : June 30, 1998
INVENTOR(S) : M. H. El Kouni, et al.

It is certified that error appears in the above-identified patent and that said Letters Patent is hereby corrected as shown below:

Biochemical Pharmacology, Vol. 41, No 5, Mahmoud H. el Kouni Efficacy of Combination Therapy with Tubercidin and Nitrobenzylthioinosine 5'-Monophosphate Against Chronic and Advanced Stages of Schistosomiasis, 1991, pp. 815-820.--

Column 21, Line 23: "Brinnmann" should read --Brinkmann--

Column 29, Line 50: "inhibihon" should read --inhibition--

Signed and Sealed this

Thirteenth Day of March, 2001

*Attest:*

NICHOLAS P. GODICI

*Attesting Officer*   *Acting Director of the United States Patent and Trademark Office*